(12) United States Patent
Waddell et al.

(10) Patent No.: US 7,915,252 B2
(45) Date of Patent: Mar. 29, 2011

(54) SULFONYL COMPOUNDS AS INHIBITORS OF 11-BETA-HYDROXYSTEROID DEHYDROGENASE-1

(75) Inventors: Sherman T. Waddell, Westfield, NJ (US); James M. Balkovec, Martinsville, NJ (US); Gina M. Santorelli, Oceanport, NJ (US); Aaron H. Leeman, Portland, ME (US); Milana Maletic, Summit, NJ (US); Xin Gu, Scotch Plains, NJ (US)

(73) Assignee: Merck Sharp & Dohme, Rahway, NJ (US)

( * ) Notice: Subject to any disclaimer, the term of this patent is extended or adjusted under 35 U.S.C. 154(b) by 709 days.

(21) Appl. No.: 11/658,766

(22) PCT Filed: Aug. 3, 2005

(86) PCT No.: PCT/US2005/027500
§ 371 (c)(1),
(2), (4) Date: Jan. 26, 2007

(87) PCT Pub. No.: WO2006/017542
PCT Pub. Date: Feb. 16, 2006

(65) Prior Publication Data
US 2008/0318930 A1    Dec. 25, 2008

Related U.S. Application Data

(60) Provisional application No. 60/599,361, filed on Aug. 6, 2004.

(51) Int. Cl.
*A61K 31/55* (2006.01)
*A61K 31/166* (2006.01)
*A61K 31/403* (2006.01)
*A61P 3/00* (2006.01)
*C07C 235/70* (2006.01)
*C07D 223/14* (2006.01)

(52) U.S. Cl. ........ 514/216; 514/412; 514/618; 564/188; 540/581

(58) Field of Classification Search .................. None
See application file for complete search history.

(56) References Cited

U.S. PATENT DOCUMENTS
6,849,636 B2    2/2005   Waddell et al.

FOREIGN PATENT DOCUMENTS
WO    WO 2004/089470    10/2004

OTHER PUBLICATIONS

Adamantane, http://en.wikipedia.org/wiki/Adamantane.*
Chawla et al., "Challenges in Polymorphism of Pharmaceuticals", CRIPS vol. 5, No. 1, Jan.-Mar. 2004 (4 Pages).*
Newman et al., "Solid-state analysis of the active pharmaceutical ingredient in drug products", DDT vol. 8, No. 19, Oct. 2003, p. 898-905.*
Treatment, http://www.ncbi.nlm.nih.gov/pubmed/12960099.*
Treatment2, http://www.ncbi.nlm.nih.gov/pubmed/12519867.*
Treatment3, http://jem.rupress.org/cgi/content/abstract/202/4/517.*
Grob et al., caplus an 1978:579314.*
Supplementary European Search Report, dated Jun. 17, 2009, Application No. EP 05 77 7427, corresponding to PCT/US05/027500.

* cited by examiner

*Primary Examiner* — Sun Jae Y Loewe
(74) *Attorney, Agent, or Firm* — Mark R. Daniel; Heidi Struse; Richard S. Parr

(57) ABSTRACT

Sulfonyl derivatives of structural formula I are selective inhibitors of the 11β-hydroxysteroid dehydrogenase-1. The compounds are useful for the treatment of diabetes, such as noninsulin-dependent diabetes (NIDDM), hyperglycemia, obesity, insulin resistance, dyslipidemia, hyperlipidemia, hypertension, Metabolic Syndrome or Syndrome X, and other symptoms associated with NIDDM.

16 Claims, No Drawings

SULFONYL COMPOUNDS AS INHIBITORS OF 11-BETA-HYDROXYSTEROID DEHYDROGENASE-1

CROSS REFERENCE TO RELATED APPLICATIONS

This application is a US National Phase application filed under 35 U.S.C. §371 based upon PCT Application Serial No PCT/US2005/027500 filed on 3 Aug. 2005, which was based upon a U.S. Provisional Application Ser. No. 60/599,361 filed on Aug. 6, 2004, priority of which is claimed hereunder.

FIELD OF THE INVENTION

The present invention relates to sulfonyl derivatives as inhibitors of the enzyme 11-beta-hydroxysteroid dehydrogenase Type I (11β-HSD-1 or HSD-1) and methods of treatment certain conditions using such compounds. The compounds of the present invention are useful for the treatment of diabetes, such as non-insulin dependent Type 2 diabetes mellitus (NIDDM), insulin resistance, obesity, lipid disorders, hypertension, and other diseases and conditions.

BACKGROUND OF THE INVENTION

Diabetes is caused by multiple factors and is most simply characterized by elevated levels of plasma glucose (hyperglycemia) in the fasting state. There are two generally recognized forms of diabetes: Type 1 diabetes, or insulin-dependent diabetes mellitus (IDDM), in which patients produce little or no insulin, the hormone which regulates glucose utilization, and Type 2 diabetes, or noninsulin-dependent diabetes mellitus (NIDDM), wherein patients produce insulin and even exhibit hyperinsulinemia (plasma insulin levels that are the same or even elevated in comparison with non-diabetic subjects), while at the same time demonstrating hyperglycemia. Type 1 diabetes is typically treated with exogenous insulin administered via injection. However, Type 2 diabetics often develop "insulin resistance", such that the effect of insulin in stimulating glucose and lipid metabolism in the main insulin-sensitive tissues, namely, muscle, liver and adipose tissues, is diminished. Patients who are insulin resistant but not diabetic have elevated insulin levels that compensate for their insulin resistance, so that serum glucose levels are not elevated. In patients with NIDDM, the plasma insulin levels, even when they are elevated, are insufficient to overcome the pronounced insulin resistance, resulting in hyperglycemia.

Insulin resistance is primarily due to a receptor binding defect that is not yet completely understood. Resistance to insulin results in insufficient activation of glucose uptake, diminished oxidation of glucose and storage of glycogen in muscle, inadequate insulin repression of lipolysis in adipose tissue and inadequate glucose production and secretion by the liver.

Persistent or uncontrolled hyperglycemia that occurs in diabetics is associated with increased morbidity and premature mortality. Abnormal glucose homeostasis is also associated both directly and indirectly with obesity, hypertension and alterations in lipid, lipoprotein and apolipoprotein metabolism. Type 2 diabetics are at increased risk of developing cardiovascular complications, e.g., atherosclerosis, coronary heart disease, stroke, peripheral vascular disease, hypertension, nephropathy, neuropathy and retinopathy. Therefore, therapeutic control of glucose homeostasis, lipid metabolism, obesity and hypertension are critically important in the clinical management and treatment of diabetes mellitus.

Many patients who have insulin resistance but have not developed Type 2 diabetes are also at a risk of developing symptoms referred to as "Metabolic Syndrome" or "Syndrome X". Metabolic Syndrome or Syndrome X is characterized by insulin resistance, along with abdominal obesity, hyperinsulinemia, high blood pressure, low HDL and high VLDL. These patients, whether or not they develop overt diabetes mellitus, are at increased risk of developing the cardiovascular complications listed above.

Treatment of Type 2 diabetes typically includes physical exercise and dieting. Increasing the plasma level of insulin by administration of sulfonylureas (e.g. tolbutamide and glipizide) or meglitinide, which stimulate the pancreatic β-cells to secrete more insulin, and/or by injection of insulin when sulfonylureas or meglitinide become ineffective, can result in insulin concentrations high enough to stimulate insulin-resistant tissues. However, dangerously low levels of plasma glucose can result, and an increased level of insulin resistance can ultimately occur.

Biguanides increase insulin sensitivity, resulting in some correction of hyperglycemia. However, many biguanides, e.g., phenformin and metformin, cause lactic acidosis, nausea and diarrhea.

The glitazones (i.e. 5-benzylthiazolidine-2,4-diones) form a newer class of compounds with the potential for ameliorating hyperglycemia and other symptoms of Type 2 diabetes. These agents substantially increase insulin sensitivity in muscle, liver and adipose tissue, resulting in partial or complete correction of the elevated plasma levels of glucose substantially without causing hypoglycemia. The glitazones that are currently marketed are agonists of the peroxisome proliferator activated receptor (PPAR) gamma subtype. PPAR-gamma agonism is generally believed to be responsible for the improved insulin sensitization that is observed with the glitazones. Newer PPAR agonists that are being developed for treatment of Type 2 diabetes and/or dyslipidemia are agonists of one or more of the PPAR alpha, gamma and delta subtypes. For a review of insulin-sensitizing agents and other mechanisms for the treatment of Type 2 diabetes, see M. Tadayyon and S. A. Smith, "Insulin sensitisation in the treatment of Type 2 diabetes," *Expert Opin. Investig. Drugs*, 12: 307-324 (2003).

There is a continuing need for new methods of treating diabetes and related conditions, such as Metabolic Syndrome or Syndrome X. The present invention meets this and other needs.

SUMMARY OF THE INVENTION

The present invention relates to sulfonyl compounds of structural formula I

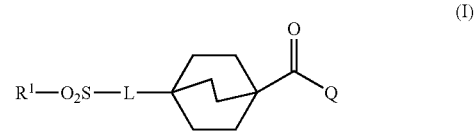

or a pharmaceutically acceptable salt thereof; wherein:

Q represents $NR^2R^3$ or a group selected from the following:

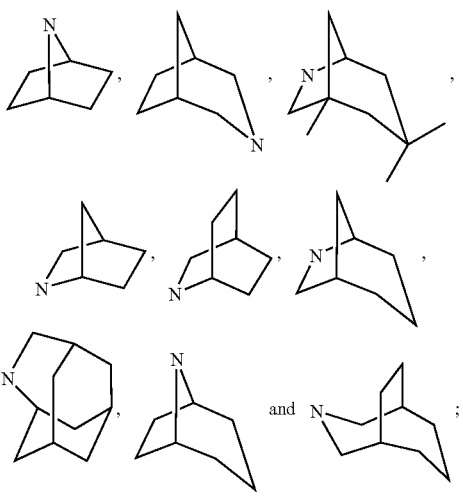

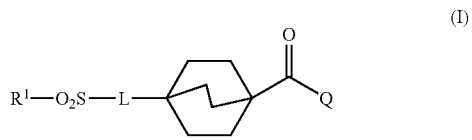

or a pharmaceutically acceptable salt thereof; wherein:
Q represents $NR^2R^3$ or a group selected from the following:

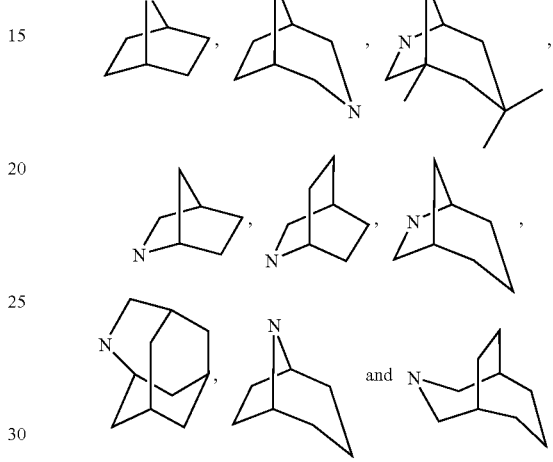

wherein said group may be optionally substituted with from one to five substituents selected from the group consisting of halo, $C_{1-3}$alkyl, $C_{1-3}$alkoxy, $C_{1-3}$haloalkyl and hydroxyl;

L represents the linking group $-(CH_2)_a-X-(CH_2)_b-$, wherein:

X represents a bond or is selected from the group consisting of: O, S, NH, $N(C_{1-3}$alkyl), C(O)NH, NHC(O), vinyl, Aryl, Aryloxy and HAR, when L is other than a bond, said group L is optionally substituted with 1-5 groups selected from: halo, cyano, $C_{1-4}$alkoxy, $C_{1-4}$alkylthio, hydroxy and amino;

said Aryl, Aryloxy and HAR groups being further optionally substituted with one to five of the following groups: halo, cyano, $C_{1-4}$alkoxy, $C_{1-4}$alkylthio, hydroxy and amino;

when X is O, S, NH or $N(C_{1-3}$alkyl), a represents an integer of from 2-6 and b represents an integer of from 0-4, such that the sum of a and b is from 2-6;

and when X is a bond, C(O)NH, NHC(O), vinyl, Aryl, Aryloxy or HAR, a and b each represent integers of from 0-6, such that the sum of a and b is 0 to 6;

$R^1$ represents a member selected from the group consisting of: $C_{1-6}$alkyl, $C_{2-6}$alkenyl, Aryl or HAR, optionally substituted with one to five of the following groups: halo, cyano, $C_{1-4}$alkoxy, $C_{1-4}$alkylthio, hydroxy, amino, Aryl and HAR, said Aryl and HAR being further optionally substituted with one to three substituents independently selected from cyano, halo, hydroxy, amino, carboxy, trifluoromethyl, trifluoromethoxy, $C_{1-4}$alkyl, and $C_{1-4}$alkoxy;

$R^2$ is H or $C_{1-3}$alkyl; and $R^3$ is a bicyclic or tricyclic alkyl moiety having 6-12 carbon atoms, optionally substituted with 1-4 substituents selected from the group consisting of $C_{1-4}$alkyl, halo, halo$C_{1-4}$alkyl, $C_{1-4}$alkoxy, halo$C_{1-4}$alkoxy, OH, $C_{1-6}$alkyl-$SO_2$— and phenyl-$SO_2$—, the alkyl and phenyl portions of $C_{1-6}$alkyl-$SO_2$— and phenyl-$SO_2$— being optionally substituted with 1-3 halo, $C_{1-3}$alkyl, halo$C_{1-3}$alkyl, $C_{1-3}$alkoxy and halo$C_{1-3}$alkoxy groups.

DETAILED DESCRIPTION OF THE INVENTION

The present invention relates to sulfonyl derivatives represented by formula I:

or a pharmaceutically acceptable salt thereof; wherein:
Q represents $NR^2R^3$ or a group selected from the following:

wherein said group may be optionally substituted with from one to five substituents selected from the group consisting of halo, $C_{1-3}$alkyl, $C_{1-3}$alkoxy, $C_{1-3}$haloalkyl and hydroxyl;

L represents the linking group $-(CH_2)_a-X-(CH_2)_b-$, wherein:

X represents a bond or is selected from the group consisting of: O, S, NH, $N(C_{1-3}$alkyl), C(O)NH, NHC(O), vinyl, Aryl, Aryloxy and HAR, when L is other than a bond, said group L is optionally substituted with 1-5 groups selected from: halo, cyano, $C_{1-4}$alkoxy, $C_{1-4}$alkylthio, hydroxy and amino;

said Aryl, Aryloxy and HAR groups being further optionally substituted with one to five of the following groups: halo, cyano, $C_{1-4}$alkoxy, $C_{1-4}$alkylthio, hydroxy and amino;

when X is O, S, NH or $N(C_{1-3}$alkyl), a represents an integer of from 2-6 and b represents an integer of from 0-4, such that the sum of a and b is from 2-6;

and when X is a bond, C(O)NH, NHC(O), vinyl, Aryl, Aryloxy or HAR, a and b each represent integers of from 0-6, such that the sum of a and b is 0 to 6;

$R^1$ represents a member selected from the group consisting of: $C_{1-6}$alkyl, $C_{2-6}$alkenyl, Aryl or HAR, optionally substituted with one to five of the following groups: halo, cyano, $C_{1-4}$alkoxy, $C_{1-4}$alkylthio, hydroxy, amino, Aryl and HAR, said Aryl and HAR being further optionally substituted with one to three substituents independently selected from cyano, halo, hydroxy, amino, carboxy, trifluoromethyl, trifluoromethoxy, $C_{1-4}$alkyl, and $C_{1-4}$alkoxy;

$R^2$ is H or $C_{1-3}$alkyl; and $R^3$ is a bicyclic or tricyclic alkyl moiety having 6-12 carbon atoms, optionally substituted with 1-4 substituents selected from the group consisting of $C_{1-4}$alkyl, halo, halo$C_{1-4}$alkyl, $C_{1-4}$alkoxy, halo$C_{1-4}$alkoxy, OH, $C_{1-4}$ alkyl-$SO_2$— and phenyl-$SO_2$—, the alkyl and phenyl portions of $C_{1-6}$alkyl-$SO_2$— and phenyl-$SO_2$— being optionally substituted with 1-3 halo, $C_{1-3}$alkyl, halo$C_{1-3}$alkyl, $C_{1-3}$alkoxy and halo$C_{1-3}$alkoxy groups.

As used herein the following definitions are applicable.

"Alkyl", and the alkyl portions of groups such as alkoxy, alkylamino, alkylsulfonyl and the like, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from $C_{3-10}$, the term alkyl also includes cycloalkyl groups, and combinations of linear or branched alkyl chains combined with cycloalkyl structures. When no number of carbon atoms is specified, $C_{1-6}$ is intended. Alkyl also includes divalent groups where appropriate, such as when L represents an "alkyl" group.

"Alkenyl" means carbon chains which contain at least one carbon-carbon double bond, and which may be linear or branched or combinations thereof, unless the carbon chain is defined otherwise. Examples of alkenyl include vinyl (or ethenyl), allyl, isopropenyl, pentenyl, hexenyl, heptenyl, 1-propenyl, 2-butenyl, 2-methyl-2-butenyl, butadienyl and the like. Where the specified number of carbon atoms permits, e.g., from $C_5$-10, the term alkenyl also includes cycloalkenyl groups, and combinations of linear, branched and cyclic structures. When no number of carbon atoms is specified, $C_{2-6}$ is intended. Alkenyl also includes divalent moieties where appropriate, e.g., where L represents a vinyl group.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl, and the like.

"Cycloalkyl" means a saturated carbocyclic ring having 3-10 or a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

"Bicycloalkyl" as used herein is a subset of cycloalkyl and means a saturated carbobicyclic ring having a specified number of carbon atoms. Examples of bicycloalkyl include bicyclo[2.1.1]hexyl, bicyclo[2.2.1]heptyl, bicyclo[2.2.2]octyl, bicyclo[3.2.1]octyl, bicyclo[3.2.2]nonyl and the like. A bicycloalkyl group is generally identified as requiring two bond scissions to produce an acyclic structure. Bicycloalkyl groups are saturated unless otherwise defined.

"Tricycloalkyl" is another subset of cycloalkyl and means a saturated carbotricyclic ring having a specified number of carbon atoms. Examples of tricycloalkyl include tricyclo[3.3.1.13.7]decyl (also commonly called adamantyl), homoadamantyl, and the like. A tricycloalkyl group is generally identified as requiring three bond scissions to produce an acyclic structure. Tricycloalkyl groups are saturated unless otherwise defined.

Exo-bornyl, endo-bornyl and 2-adamantyl have the following structural formulas:

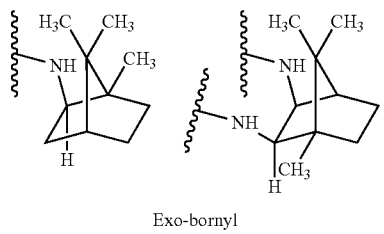

Exo-bornyl

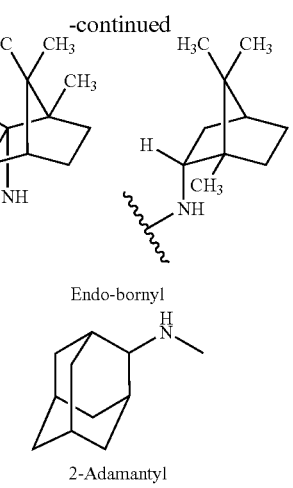

Endo-bornyl

2-Adamantyl

As shown above, exo- and endo-bornyl each have isomers. All such isomers are included in the compounds of the present invention. When Q represents one of the bi- or tricyclic structures shown, it is attached through the heterocyclic N atom.

A commonly accepted definition of "Metabolic Syndrome or Syndrome X" is the presence of at least three of the four conditions which follow: 1) fasting glucose greater than 110 mg/dL; 2) blood pressure higher than 130/85 mm Hg; 3) waist circumference greater than 102 cm for men or 85 cm for women; 4) circulating triglycerides greater than 150 mg/dL for both men and women and HDL-C less than 40 mg/dL for men or less than 50 mg/dL for women.

The term "alkoxy" refers to straight or branched chain alkoxides of the number of carbon atoms specified (e.g., $C_{1-6}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-6}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl (MeSO$_2$—), ethylsulfonyl, isopropylsulfonyl, etc.].

The term "alkylsulfinyl" refers to straight or branched chain alkylsulfoxides of the number of carbon atoms specified (e.g., $C_{1-6}$ alkylsulfinyl), or any number within this range [i.e., methylsulfinyl (MeSO—), ethylsulfinyl, isopropylsulfinyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" and the aryl portion of aryloxy mean a mono- or polycyclic aromatic ring system containing carbon ring atoms, which are mono- or divalent as appropriate. The preferred aryls are monocyclic or bicyclic 6-10 carbon aromatic ring systems. Phenyl and naphthyl are preferred aryls. The most preferred aryl is phenyl. When X represents aryloxy, this means that L represents the following: —(CH$_2$)$_a$-aryloxy-(CH$_2$)$_b$—.

"Heterocycle" and "heterocyclyl" refer to saturated or unsaturated non-aromatic rings or ring systems containing 4-15 atoms and at least one heteroatom selected from O, S and N, further including the oxidized forms of sulfur, namely SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

"Heteroaryl" (HAR) means an aromatic or partially aromatic heterocycle that contains 5-15 atoms and at least one ring heteroatom selected from O, S and N. It can be mono- or di-valent as appropriate. Heteroaryls thus includes heteroaryls fused to other kinds of rings, such as aryls, cycloalkyls and heterocycles that are not aromatic. Examples of heteroaryl groups include: pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, and the like. For heterocyclyl and heteroaryl groups, rings and ring systems containing from 3-15 atoms are included, forming 1-3 rings.

"Halogen" and "halo" refer to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$). Haloalkyl means that from 1-6 halo groups are substituted on alkyl, up to perhaloalkyl. Similarly, haloalkoxy means that from 1-6 halo groups are substituted on the alkyl portion of alkoxy, up to a perhaloalkoxy group.

The term "pharmaceutical composition" encompasses a product comprising the active ingredient(s), and the inert ingredient(s) that make up the carrier, as well as any product which results, directly or indirectly, from combination, complexation or aggregation of any two or more of the ingredients, or from a dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The terms "administration of" and "administering" a compound should be understood to mean providing a compound of the invention or a prodrug of a compound of the invention to the individual in need.

The compounds described herein are effective as inhibitors of 11β-hydroxysteroid dehydrogenase type 1 (11β-HSD1). They are therefore useful for the treatment, control or prevention of disorders responsive to the inhibition of 11β-HSD1, such as Type 2 diabetes, lipid disorders, obesity, atherosclerosis, and Metabolic Syndrome or Syndrome X.

A subset of compounds that is of interest relates to compounds of formula I or a salt or solvate thereof wherein Q represents $NR^2R^3$. Within this subset, all other variables are as originally defined with respect to formula I.

Another subset of compounds that is of interest relates to compounds of formula I or a salt or solvate thereof wherein Q represents a member selected from the group consisting of:

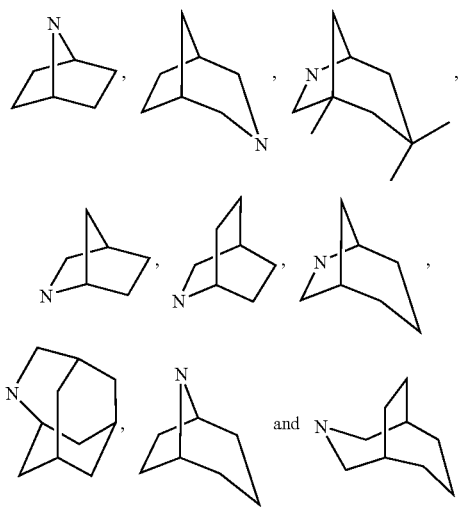

said group being optionally substituted with from one to five substituents selected from the group consisting of halo, $C_{1-3}$alkyl, $C_{1-3}$alkoxy, $C_{1-3}$haloalkyl and hydroxyl. Within this subset, all other variables are as originally defined.

Another subset of compounds that is of interest relates to compounds of formula I or a salt or solvate thereof, wherein $R^1$ represents a $C_{1-4}$alkyl group optionally substituted with 1-3 fluoro groups, or a phenyl group optionally substituted with 1-2 halo, $C_{1-3}$alkyl, mono-, di- or tri-fluoro$C_{1-3}$alkyl or mono-, di- or tri-fluoro$C_{1-3}$alkoxy groups. Within this subset, all other variables are as originally defined with respect to formula I.

More particularly, compounds that are of interest include compounds of formula I as well as salts and solvates thereof, wherein $R^1$ represents methyl, ethyl, trifluoromethyl, isopropyl, t-butyl, 2,2,2-trifluoroethyl or phenyl optionally substituted with halo, methyl, trifluoromethyl or trifluoromethoxy. Within this subset, all other variables are as originally defined with respect to formula I.

A subset of compounds that is of interest relates to a compound of formula I:

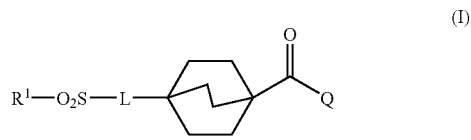

(I)

or a pharmaceutically acceptable salt thereof; wherein:

Q represents $NR^2R^3$ or a group selected from the following:

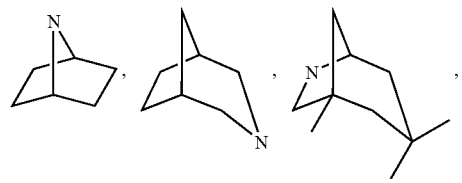

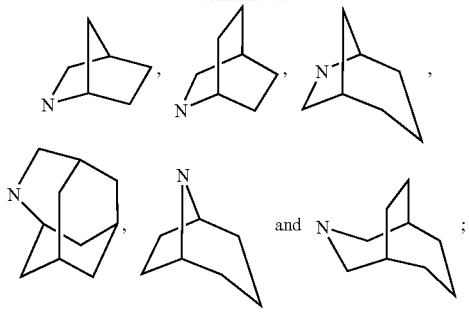

wherein said group may be optionally substituted with from one to five substituents selected from the group consisting of halo, $C_{1-3}$alkyl, $C_{1-3}$alkoxy, $C_{1-3}$haloalkyl and hydroxyl;

L represents the linking group $—(CH_2)_a—X—(CH_2)_b—$, wherein:

X represents a bond or is selected from the group consisting of: O, S, NH, N($C_{1-3}$alkyl), C(O)NH, NHC(O), vinyl, Aryl, Aryloxy and HAR, when L is other than a bond, said group L is optionally substituted with 1-5 groups selected from: halo, cyano, $C_{1-4}$alkoxy, $C_{1-4}$alkylthio, hydroxy and amino;

said Aryl, Aryloxy and HAR groups being further optionally substituted with one to five of the following groups: halo, cyano, $C_{1-4}$alkoxy, $C_{1-4}$alkylthio, hydroxy and amino;

when X is O, S, NH or N($C_{1-3}$alkyl), a represents an integer of from 2-6 and b represents an integer of from 0-4, such that the sum of a and b is from 2-6;

and when X is a bond, C(O)NH, NHC(O), vinyl, Aryl, Aryloxy or HAR, a and b each represent integers of from 0-6, such that the sum of a and b is 0 to 6;

$R^1$ represents a member selected from the group consisting of: $C_{1-6}$alkyl or $C_{2-6}$alkenyl, optionally substituted with one to five of the following groups: halo, cyano, $C_{1-4}$alkoxy, $C_{1-4}$alkylthio, hydroxy, amino, Aryl and HAR, said Aryl and HAR being further optionally substituted with one to three substituents independently selected from cyano, halo, hydroxy, amino, carboxy, trifluoromethyl, trifluoromethoxy, $C_{1-4}$alkyl, and $C_{1-4}$alkoxy;

$R^2$ is H or $C_{1-3}$alkyl; and $R^3$ is a bicyclic or tricyclic alkyl moiety having 6-12 carbon atoms, optionally substituted with 1-4 substituents selected from the group consisting of $C_{1-4}$alkyl, halo, halo$C_{1-4}$alkyl, $C_{1-4}$alkoxy, halo$C_{1-4}$alkoxy, OH, $C_{1-4}$alkyl-$SO_2$— and phenyl-$SO_2$—, the alkyl and phenyl portions of $C_{1-6}$alkyl-$SO_2$— and phenyl-$SO_2$— being optionally substituted with 1-3 halo, $C_{1-3}$alkyl, halo$C_{1-3}$alkyl, $C_{1-3}$alkoxy and halo$C_{1-3}$alkoxy groups.

Another subset of compounds that is of interest relates to compounds of formula I:

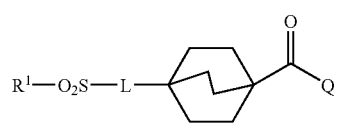

(I)

or a pharmaceutically acceptable salt thereof; wherein:

Q represents $NR^2R^3$ or a group selected from the following:

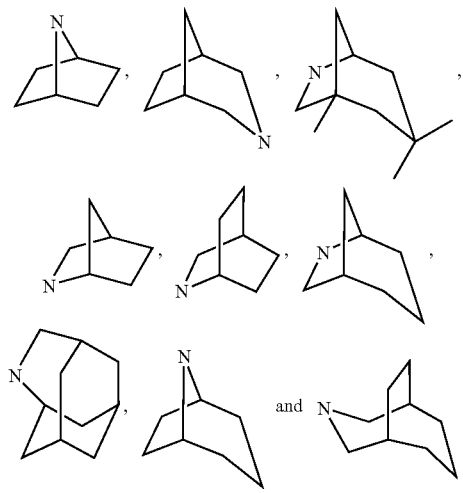

wherein said group may be optionally substituted with from one to five substituents selected from the group consisting of halo, $C_{1-3}$alkyl, $C_{1-3}$alkoxy, $C_{1-3}$haloalkyl and hydroxyl;

L represents the linking group $—(CH_2)_a—X—(CH_2)_b—$, wherein:

X represents a bond or is selected from the group consisting of: O, S, NH, N($C_{1-3}$alkyl), C(O)NH, NHC(O), vinyl, Aryl, Aryloxy and HAR, when L is other than a bond, said group L is optionally substituted with 1-5 groups selected from: halo, cyano, $C_{1-4}$alkoxy, $C_{1-4}$alkylthio, hydroxy and amino;

said Aryl, Aryloxy and HAR groups being further optionally substituted with one to five of the following groups: halo, cyano, $C_{1-4}$alkoxy, $C_{1-4}$alkylthio, hydroxy and amino;

when X is O, S, NH or N($C_{1-3}$alkyl), a represents an integer of from 2-6 and b represents an integer of from 0-4, such that the sum of a and b is from 2-6;

and when X is a bond, C(O)NH, NHC(O), vinyl, Aryl, Aryloxy or HAR, a and b each represent integers of from 0-6, such that the sum of a and b is 0 to 6;

$R^1$ represents a member selected from the group consisting of: Aryl or HAR, optionally substituted with one to five of the following groups: halo, cyano, $C_{1-4}$alkoxy, $C_{1-4}$alkylthio, hydroxy, amino, Aryl and HAR, said Aryl and HAR each being further optionally substituted with one to three substituents independently selected from cyano, halo, hydroxy, amino, carboxy, trifluoromethyl, trifluoromethoxy, $C_{1-4}$alkyl, and $C_{1-4}$alkoxy;

$R^2$ is H or $C_{1-3}$alkyl; and $R^3$ is a bicyclic or tricyclic alkyl moiety having 6-12 carbon atoms, optionally substituted with 1-4 substituents selected from the group consisting of $C_{1-4}$alkyl, halo, halo$C_{1-4}$alkyl, $C_{1-4}$alkoxy, halo$C_{1-4}$alkoxy, OH, $C_{1-6}$alkyl-$SO_2$— and phenyl-$SO_2$—, the alkyl and phenyl portions of $C_{1-6}$alkyl-$SO_2$— and phenyl-$SO_2$— being optionally substituted with 1-3 halo, $C_{1-3}$alkyl, halo$C_{1-3}$alkyl, $C_{1-3}$alkoxy and halo$C_{1-3}$alkoxy groups.

Another subset of compounds that is of interest relates to compounds of formula I as well as salts and solvates thereof, wherein:

L represents $—(CH_2)_a—X—(CH_2)_b—$,

X represents a bond, O, S, Aryl, Aryloxy or HAR;

when X represents O or S, a equals 2, 3 or 4, and b equals 0-4 such that the sum of a plus b is 2 to 6, and when X represents a bond, Aryl, Aryloxy or HAR, a and b are each 0-6 such that the sum of a plus b is 0 to 6. Within this subset of the invention, all other variables are as originally defined.

Another subset of compounds that is of interest relates to compounds of formula I as well as salts and solvates thereof, wherein L is selected from the group consisting of: methylene, ethylene, propylene, butylene and 1,4-phenylene. Within this subset of the invention, all other variables are as originally defined.

Another subset of compounds that is of interest relates to compounds of formula I as well as salts and solvates thereof, wherein Q represents $NR^2R^3$ or is selected from the group consisting of:

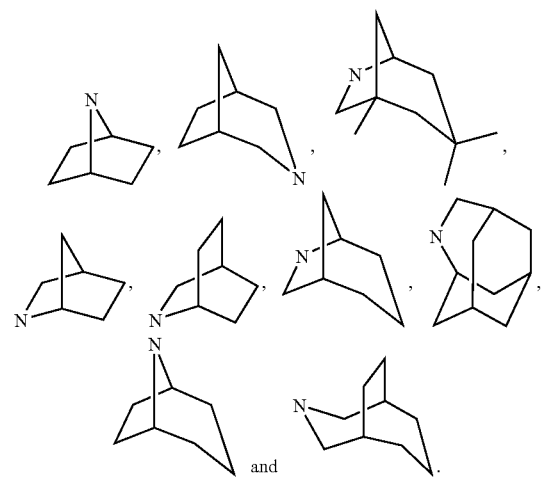

Within this subset, all other variables are as originally defined with respect to formula I.

Another subset of compounds that is of interest relates to compounds of formula I or a salt or solvate thereof, wherein Q represents $NR^2R^3$. Within this subset, all other variables are as originally defined with respect to formula I.

Even more particularly, compounds that are of interest include those compounds of formula I or a salt or solvate thereof, $R^2$=H and, wherein Q represents $NR^2R^3$, $R^2$ represents H and $R^3$ represents a bicyclic or tricyclic alkyl moiety having 6-12 carbon atoms, optionally substituted with 1-3 members selected from the group consisting of: $CH_3$, fluoro, chloro, $CF_3$, $OCH_3$, $OCF_3$, and $CH_3SO_2$. Within this subset, all other variables are as originally defined with respect to formula I.

Even more particularly, compounds that are of interest include compounds of formula I or a salt or solvate thereof wherein $R^2$ equals H and $R^3$ represents 2-adamantyl or exo-bornyl. Within this subset, all other variables are as originally defined with respect to formula I.

More particularly, a subset of compounds of the present invention is described as including compounds of formula I or a salt or solvate thereof, wherein:

$R^1$ represents a $C_{1-4}$alkyl group optionally substituted with 1-3 fluoro groups, or a phenyl group optionally substituted with 1-2 halo, $C_{1-3}$alkyl, mono-, di- or tri-fluoro$C_{1-3}$alkyl or mono-, di- or tri-fluoro$C_{1-3}$alkoxy groups;

L represents —$(CH_2)_a$—X—$(CH_2)_b$—,

X represents a bond, O, S, Aryl, Aryloxy or HAR;

when X represents O or S, a equals 2, 3 or 4, and b equals 0-4 such that the sum of a plus b is 2-6, and when X is a bond, Aryl, Aryloxy or HAR, a and b are each 0-6 such that the sum of a plus b is 0 to 6;

Q represents $NR^2R^3$ or is selected from the group consisting of:

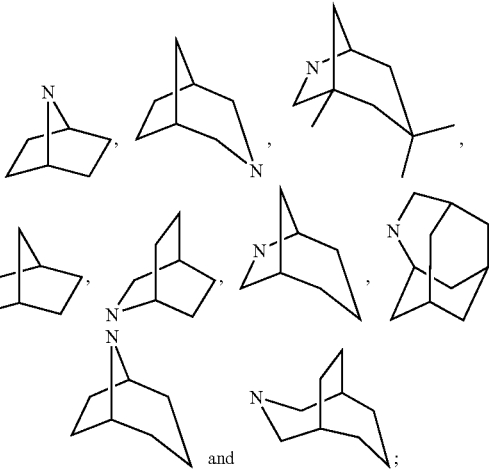

$R^2$ represents H and $R^3$ represents a bicyclic or tricyclic alkyl moiety having 6-12 carbon atoms, optionally substituted with 1-3 members selected from the group consisting of: $CH_3$, fluoro, chloro, $CF_3$, $OCH_3$, $OCF_3$, and $CH_3SO_2$. Within this subset, all other variables are as originally defined with respect to formula I.

More particularly, compounds that are of interest include compounds of formula I, or a salt or solvate thereof, wherein:

$R^1$ represents methyl, ethyl, isopropyl, t-butyl, trifluoromethyl, 2,2,2-trifluoroethyl or phenyl optionally substituted with halo, methyl, trifluoromethyl or trifluoromethoxy;

L is selected from the group consisting of: methylene, ethylene, propylene, butylene and 1,4-phenylene, Q represents $NR^2R^3$;

$R^2$ represents H and $R^3$ represents a bicyclic or tricyclic alkyl moiety having 6-12 carbon atoms, optionally substituted with 1-3 members selected from the group consisting of: $CH_3$, fluoro, chloro, $CF_3$, $OCH_3$, $OCF_3$, and $CH_3SO_2$. Within this subset, all other variables are as originally defined with respect to formula I.

Species falling within the scope of the invention are described in the examples provided below.

The present invention also relates to pharmaceutical compositions comprising the compounds of the present invention and a pharmaceutically acceptable carrier.

The present invention also relates to methods for the treatment, control, or prevention of disorders, diseases, or conditions responsive to inhibition of 11β-HSD1 in a subject in need thereof by administering the compounds and pharmaceutical compositions of the present invention.

The present invention also relates to methods for the treatment or control of Type 2 diabetes, obesity, lipid disorders, atherosclerosis or Metabolic Syndrome or Syndrome X by administering the compounds and pharmaceutical compositions of the present invention.

The present invention also relates to methods for treating obesity by administering the compounds of the present invention in combination with a therapeutically effective amount of another agent known to be useful to treat the condition.

The present invention also relates to methods for treating Type 2 diabetes by administering the compounds of the present invention in combination with a therapeutically effective amount of another agent known to be useful to treat the condition.

The present invention also relates to methods for treating atherosclerosis by administering the compounds of the present invention in combination with a therapeutically effective amount of another agent known to be useful to treat the condition.

The present invention also relates to methods for treating lipid disorders by administering the compounds of the present invention in combination with a therapeutically effective amount of another agent known to be useful to treat the condition.

The present invention also relates to methods for treating Metabolic Syndrome or Syndrome X by administering the compounds of the present invention in combination with a therapeutically effective amount of another agent known to be useful to treat the condition.

The present invention is also concerned with the use of the compounds of structural formula I for the treatment hyperglycemia, insulin resistance, Type 2 diabetes, lipid disorders, obesity, atherosclerosis, and Metabolic Syndrome or Syndrome X.

The present invention also provides for the use of the compounds of structural formula I in the manufacture of a medicament for use in the treatment of hyperglycemia, insulin resistance, Type 2 diabetes, lipid disorders, obesity, atherosclerosis, and Metabolic Syndrome or Syndrome X.

Compounds of structural formula I may contain one or more asymmetric centers and can thus occur as racemates and racemic mixtures, single enantiomers, diastereomeric mixtures and individual diastereomers. The present invention includes all such isomeric forms of the compounds of structural formula I.

Some of the compounds described herein contain an olefinic double bond. The invention includes both E and Z geometric isomers.

Some of the compounds described herein may exist as tautomers such as keto-enol tautomers. The individual tautomers, as well as mixtures thereof, are encompassed within the invention.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, a stereoisomer of a compound of the general structural formula I may be obtained by stereospecific synthesis using optically pure starting materials or reagents of known absolute configuration.

In a different aspect of the invention, a pharmaceutical composition is addressed comprising a compound in accordance with structural formula I, or a pharmaceutically acceptable salt or solvate thereof, in combination with a pharmaceutically acceptable carrier. By the term "solvate" is meant a hydrate, an alcoholate, or other solvent of crystallization.

In another aspect of the invention, a method of treating hyperglycemia, diabetes or insulin resistance in a mammalian patient in need of such treatment is addressed, which comprises administering to said patient an effective amount of a compound in accordance with structural formula I or a pharmaceutical salt or solvate thereof.

In another aspect of the invention, a method of treating non-insulin dependent (Type 2) diabetes mellitus in a mammalian patient in need of such treatment is disclosed comprising administering to the patient an anti-diabetic effective amount of a compound in accordance with structural formula I.

In another aspect of the invention, a method of treating obesity in a mammalian patient in need of such treatment is disclosed comprising administering to said patient a compound in accordance with structural formula I in an amount that is effective to treat obesity.

In another aspect of the invention, a method of treating Metabolic Syndrome or Syndrome X in a mammalian patient in need of such treatment is disclosed, comprising administering to said patient a compound in accordance with structural formula I in an amount that is effective to treat Metabolic Syndrome or Syndrome X.

In another aspect of the invention, a method of treating a lipid disorder selected from the group consisting of dyslipidemia, hyperlipidemia, hypertriglyceridemia, hypercholesterolemia, low HDL, and high LDL in a mammalian patient in need of such treatment is disclosed, comprising administering to said patient a compound in accordance with structural formula I in an amount that is effective to treat said lipid disorder.

In another aspect of the invention, a method of treating atherosclerosis in a mammalian patient in need of such treatment is disclosed, comprising administering to said patient a compound in accordance with structural formula I in an amount effective to treat atherosclerosis.

In another aspect of the invention, a method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome or Syndrome X, (21) hypertension (22) cognitive dysfunction, (23) glaucoma, (24) depression, (25) anxiety and other conditions and disorders where insulin resistance is a component or HSD-1 inhibition is appropriate, in a mammalian patient in need of such treatment is disclosed, comprising administering to the patient a compound in accordance with structural formula I in an amount that is effective to treat said condition.

In another aspect of the invention, a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome or Syndrome X, (21) hypertension, (22) cognitive dysfunction, (23) glaucoma, (24) depression, (25) anxiety and other conditions and disorders where insulin resistance is a component or HSD-1 inhibition is appropriate, in a mammalian patient in need of such treatment is disclosed, comprising administering to the patient a compound in accordance with structural formula I in an amount that is effective to delay the onset of said condition.

In another aspect of the invention, a method of reducing the risk of developing a condition selected from the group consisting of (1) hyperglycemia, (2) low glucose tolerance, (3)

insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome or Syndrome X, (21) hypertension, (22) cognitive dysfunction, (23) glaucoma, (24) depression, (25) anxiety and other conditions and disorders where insulin resistance is a component or HSD-1 inhibition is appropriate, in a mammalian patient in need of such treatment is disclosed, comprising administering to the patient a compound in accordance with structural formula I in an amount that is effective to reduce the risk of developing said condition.

In another aspect of the invention, a method of treating a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome or Syndrome X, (21) hypertension, (22) cognitive dysfunction, (23) glaucoma, (24) depression, (25) anxiety and other conditions and disorders where insulin resistance is a component or HSD-1 inhibition is appropriate, in a mammalian patient in need of such treatment, comprising administering to the patient an effective amount of a compound as defined in structural formula I and a compound selected from the group consisting of:

(a) dipeptidyl peptidase-IV (DP-IV) inhibitors;
(b) insulin sensitizing agents selected from the group consisting of (i) PPARγ agonists, (ii) PPARα agonists, (iii) PPARα/γ dual agonists, and (iv) biguanides;
(c) insulin and insulin mimetics;
(d) sulfonylureas and other insulin secretagogues;
(e) α-glucosidase inhibitors;
(f) glucagon receptor antagonists;
(g) GLP-1, GLP-1 analogs, and GLP-1 receptor agonists;
(h) GIP, GIP mimetics, and GIP receptor agonists;
(i) PACAP, PACAP mimetics, and PACAP receptor 3 agonists;
(j) cholesterol lowering agents selected from the group consisting of
  (i) HMG-CoA reductase inhibitors, (ii) sequestrants, (iii) nicotinyl alcohol, nicotinic acid and salts thereof, (iv) inhibitors of cholesterol absorption, (v) acyl CoA:cholesterol acyltransferase inhibitors, and (vi) anti-oxidants;
(k) PPARδ agonists;
(l) antiobesity compounds such as NPY 5 and CB 1 modulators;
(m) ileal bile acid transporter inhibitors;
(n) anti-inflammatory agents, excluding glucocorticoids;
(o) protein tyrosine phosphatase 1B (PTP-1B) inhibitors; and
(p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan; said compounds being administered to the patient in an amount that is effective to treat said condition.

Dipeptidyl peptidase-IV inhibitors that can be combined with compounds of structural formula I include those disclosed in WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); and WO 03/000181 (3 Jan. 2003). Specific DP-IV inhibitor compounds include isoleucine thiazolidide; NVP-DPP728; P32/98; and LAF 237.

Antiobesity compounds that can be combined with compounds of structural formula I include fenfluramine, dexfenfluramine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, and melanin-concentrating hormone (MCH) receptor antagonists. For a review of anti-obesity compounds that can be combined with compounds of structural formula I, see S. Chaki et al., "Recent advances in feeding suppressing agents: potential therapeutic strategy for the treatment of obesity," *Expert Opin. Ther. Patents*, 11: 1677-1692 (2001)

Neuropeptide Y5 antagonists that can be combined with compounds of structural formula I include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. Nos. 5,532,237; and 5,292,736.

Melanocortin receptor agonists that can be combined with compounds of structural formula I include those disclosed in WO 03/009847 (6 Feb. 2003); WO 02/068388 (6 Sep. 2002); WO 99/64002 (16 Dec. 1999); WO 00/74679 (14 Dec. 2000); WO 01/70708 (27 Sep. 2001); and WO 01/70337 (27 Sep. 2001) as well as those disclosed in J. D. Speake et al., "Recent advances in the development of melanocortin-4 receptor agonists, *Expert Opin. Ther. Patents*, 12: 1631-1638 (2002).

In another aspect of the invention, a method of treating a condition selected from the group consisting of hypercholesterolemia, atherosclerosis, low HDL levels, high LDL levels, hyperlipidemia, hypertriglyceridemia, and dyslipidemia, in a mammalian patient in need of such treatment is disclosed, comprising administering to the patient a therapeutically effective amount of a compound as defined in structural formula I and an HMG-CoA reductase inhibitor.

More particularly, in another aspect of the invention, a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment is disclosed, wherein the HMG-CoA reductase inhibitor is a statin.

Even more particularly, in another aspect of the invention, a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment is disclosed, wherein the HMG-CoA reductase inhibitor is a statin selected from the group consisting of lovastatin, simvastatin, pravastatin, cerivastatin, fluvastatin, atorvastatin, itavastatin, and rosuvastatin.

In another aspect of the invention, a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions is disclosed comprising administering to a mammalian patient in need of such treatment a therapeutically effective amount of a compound as defined in structural formula I and an HMG-CoA reductase inhibitor.

In another aspect of the invention, a method for delaying the onset or reducing the risk of developing atherosclerosis in a human patient in need of such treatment is disclosed comprising administering to said patient an effective amount of a compound as defined in structural formula I and an HMG-CoA reductase inhibitor.

More particularly, a method for delaying the onset or reducing the risk of developing atherosclerosis in a human patient in need of such treatment is disclosed, wherein the HMG-CoA reductase inhibitor is a statin.

Even more particularly, a method for delaying the onset or reducing the risk of developing atherosclerosis in a human patient in need of such treatment is disclosed, wherein the HMG-CoA reductase inhibitor is a statin selected from the group consisting of: lovastatin, simvastatin, pravastatin, cerivastatin, fluvastatin, atorvastatin, itavastatin, and rosuvastatin.

Even more particularly, a method for delaying the onset or reducing the risk of developing atherosclerosis in a human patient in need of such treatment is disclosed, wherein the statin is simvastatin.

In another aspect of the invention, a method for delaying the onset or reducing the risk of developing atherosclerosis in a human patient in need of such treatment is disclosed, wherein the HMG-CoA reductase inhibitor is a statin and further comprising administering a cholesterol absorption inhibitor.

More particularly, in another aspect of the invention, a method for delaying the onset or reducing the risk of developing atherosclerosis in a human patient in need of such treatment is disclosed, wherein the HMG-CoA reductase inhibitor is a statin and the cholesterol absorption inhibitor is ezetimibe.

In another aspect of the invention, a pharmaceutical composition is disclosed which comprises
(1) a compound according to structural formula I,
(2) a compound selected from the group consisting of:
  (a) DP-IV inhibitors;
  (b) insulin sensitizing agents selected from the group consisting of (i) PPARγ agonists; (ii) PPARα agonists, (iii) PPARα/γ dual agonists, and (iv) biguanides;
  (c) insulin and insulin mimetics;
  (d) sulfonylureas and other insulin secretagogues;
  (e) α-glucosidase inhibitors;
  (f) glucagon receptor antagonists;
  (g) GLP-1, GLP-1 analogs, and GLP-1 receptor agonists;
  (h) GIP, GIP mimetics, and GIP receptor agonists;
  (i) PACAP, PACAP mimetics, and PACAP receptor 3 agonists;
  j) cholesterol lowering agents selected from the group consisting of (i) HMG-CoA reductase inhibitors, (ii) sequestrants, (iii) nicotinyl alcohol, nicotinic acid or a salt thereof, (iv) inhibitors of cholesterol absorption, (v) acyl CoA:cholesterol acyltransferase inhibitors, and (vi) anti-oxidants;
  (k) PPARδ agonists;
  (l) antiobesity compounds;
  (m) ileal bile acid transporter inhibitors;
  (n) anti-inflammatory agents other than glucocorticoids;
  (o) protein tyrosine phosphatase 1B (PTP-1B) inhibitors; and
  (p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan; and
(3) a pharmaceutically acceptable carrier.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetate or maleate, can be employed. Included are those esters and acyl groups known in the art for modifying the solubility or hydrolysis characteristics for use as sustained-release or prodrug formulations.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

Solvates, and in particular, the hydrates of the compounds of structural formula I are included in the present invention as well.

The compounds described herein are selective inhibitors of the 11β-HSD1 enzyme. Thus, the present invention relates to the use of the 11β-HSD1 inhibitors for inhibiting the reductase activity of 11β-hydroxysteroid dehydrogenase, which is responsible for the conversion of cortisone to cortisol. Excess cortisol is associated with numerous disorders, including NIDDM, obesity, dyslipidemia, insulin resistance and hypertension. Administration of the compounds of the present invention decreases the level of cortisol and other 11β-hydroxysteroids in target tissues, thereby reducing the effects of excessive amounts of cortisol and other 11β-hydroxysteroids. Inhibition of 11β-HSD1 can be used to treat and control diseases mediated by abnormally high levels of cortisol and other 11β-hydroxysteroids, such as NIDDM, obesity, hypertension and dyslipidemia. Inhibition of 11β-HSD1 activity in the brain such as to lower cortisol levels may also be useful to treat or reduce anxiety, depression, and cognitive impairment.

The present invention includes the use of an 11β-HSD1 inhibitor for the treatment, control, amelioration, prevention, delaying the onset of or reducing the risk of developing the diseases and conditions that are described herein, as mediated by excess or uncontrolled amounts of cortisol and/or other corticosteroids in a mammalian patient, particularly a human, by the administration of an effective amount of a compound of structural formula I or a pharmaceutically acceptable salt or solvate thereof. Inhibition of the 11β-HSD1 enzyme limits the conversion of cortisone, which is normally inert, to cortisol, which can cause or contribute to the symptoms of these diseases and conditions if present in excessive amounts.

NDDM and Hypertension:

The compounds of this invention are selective inhibitors of 11β-HSD1 over 11β-HSD2. While the inhibition of 11β-HSD1 is useful for reducing cortisol levels and treating conditions related thereto, inhibition of 11β-HSD2 is associated with serious side effects, such as hypertension.

Cortisol is an important and well recognized anti-inflammatory hormone, which also acts as an antagonist to the action of insulin in the liver, such that insulin sensitivity is reduced, resulting in increased gluconeogenesis and elevated levels of glucose in the liver. Patients who already have impaired glucose tolerance have a greater probability of developing Type 2 diabetes in the presence of abnormally high levels of cortisol.

High levels of cortisol in tissues where the mineralocorticoid receptor is present often lead to hypertension. Inhibition of 11β-HSD1 shifts the ratio of cortisol and cortisone in specific tissues in favor of cortisone.

Administration of a therapeutically effective amount of an 11β-HSD1 inhibitor is effective in treating, controlling and ameliorating the symptoms of NIDDM, and administration of a therapeutically effective amount of an 11β-HSD1 inhibitor on a regular basis delays or prevents the onset of NIDDM, particularly in humans.

Cushing's Syndrome:

The effect of elevated levels of cortisol is also observed in patients who have Cushing's Syndrome, which is a metabolic disease characterized by high levels of cortisol in the blood stream. Patients with Cushing's Syndrome often develop NIDDM.

Obesity Metabolic Syndrome or Syndrome X, Dyslipidemia:

Excessive levels of cortisol have been associated with obesity, perhaps due to increased hepatic gluconeogenesis. Abdominal obesity is closely associated with glucose intolerance, hyperinsulinemia, hypertriglyceridemia, and other factors of Metabolic Syndrome or Syndrome X, such as high blood pressure, elevated VLDL and reduced HDL. Montague et al., *Diabetes,* 2000, 49: 883-888. Thus, the administration of an effective amount of an 11β-HSD1 inhibitor is useful in the treatment or control of obesity. Long-term treatment with an 11β-HSD1 inhibitor is also useful in delaying or preventing the onset of obesity, especially if the patient uses an 11β-HSD1 inhibitor in combination with controlled diet and exercise.

By reducing insulin resistance and maintaining serum glucose at normal concentrations, compounds of the present invention also have utility in the treatment and prevention of conditions that accompany Type II diabetes and insulin resistance, including the Metabolic Syndrome or Syndrome X or Syndrome X, obesity, reactive hypoglycemia and diabetic dyslipidemia.

Cognition and Dementia:

Excessive levels of cortisol in the brain may also result in neuronal loss or dysfunction through the potentiation of neurotoxins. Cognitive impairment has been associated with aging, and excess levels of cortisol in the brain. See J. R. Seckl and B. R. Walker, *Endocrinology,* 2001, 142: 1371-1376, and references cited therein. Administration of an effective amount of an 11β-HSD1 inhibitor results in the reduction, amelioration, control or prevention of cognitive impairment associated with aging and of neuronal dysfunction. Inhibitors of 11β-HSD1 may also be useful to treat anxiety and depression.

Atherosclerosis and Hypertension:

As described above, inhibition of 11β-HSD1 activity and a reduction in the amount of cortisol are beneficial in treating or controlling hypertension. Since hypertension and dyslipidemia contribute to the development of atherosclerosis, administration of a therapeutically effective amount of an 11β-HSD1 inhibitor of the present invention may be especially beneficial in treating, controlling, delaying the onset of or preventing atherosclerosis.

Effects on Pancreas:

Inhibition of 11β-HSD1 activity in isolated murine pancreatic β-cells improves glucose stimulated insulin secretion (B. Davani et al., J. Biol. Chem., 2000, 275: 34841-34844). Glucocorticoids have been shown to reduce insulin secretion in vivo. (B. Billaudel et al., Horm. Metab. Res., 1979, 11: 555-560).

Reduction of Intraocular Pressure:

Recent data suggests a connection between the levels of glucocorticoid target receptors and the 11β-HSD enzymes and the susceptibility to glaucoma (J. Stokes et al., Invest. Ophthamol., 2000, 41: 1629-1638). Therefore, inhibition of 11β-HSD1 activity is useful in reducing intraocular pressure in the treatment of glaucoma.

Immunomodulation:

In certain disease states, such as tuberculosis, psoriasis, and even under conditions of excessive stress, high glucocorticoid activity shifts the immune response to a humoral response, when in fact a cell based response may be more beneficial to the patient. Inhibition of 11β-HSD1 activity and the attendant reduction in glucocorticoid levels shifts the immune response toward a cell based response. See D. Mason, Immunology Today, 1991, 12: 57-60, and G. A. W. Rook, Baillièr's Clin. Endocrinol. Metab., 1999, 13: 576-581.

Osteoporosis:

Glucocorticoids can inhibit bone formation, which can result in a net bone loss. 11β-HSD1 has a role in bone resorption. Inhibition of 11β-HSD1 is beneficial in preventing bone loss due to osteoporosis. See C. H. Kim et al., J. Endocrinol., 1999, 162: 371-379; C. G. Bellows et al., Bone, 1998, 23: 119-125; and M. S. Cooper et al., Bone, 2000, 27: 375-381.
Other Utilities:

The following diseases, disorders and conditions can be treated, controlled, prevented or delayed, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome or Syndrome X, (21) hypertension, (22) cognitive disorders, (23) glaucoma, (24) depression, (25) anxiety and other disorders where insulin resistance is a component or inhibition of HSD-1 is appropriate.

The above diseases and conditions can be treated using the compounds of structural formula I, or the compound can be administered to prevent or reduce the risk of developing the diseases and conditions described herein. Since concurrent inhibition of 11β-HSD2 may have deleterious side effects or may actually increase the amount of cortisol in the target tissue where reduction of cortisol is desired, selective inhibitors of 11β-HSD1 with little or no inhibition of 11β-HSD2 are desirable.

The 11β-HSD1 inhibitors of structural formula I generally have an inhibition constant $IC_{50}$ of less than about 500 nM, and preferably less than about 100 nM. Generally, the $IC_{50}$ ratio for 11β-HSD2 to 11β-HSD1 of a compound is at least about two or more, and preferably about ten or greater. Even more preferred are compounds with an $IC_{50}$ ratio for 11β-HSD2 to 11β-HSD1 of about 100 or greater. For example, compounds of the present invention ideally demonstrate an inhibition constant $IC_{50}$ against 11β-HSD2 greater than about 1000 nM, and preferably greater than 5000 nM.

Compounds of structural formula I may be used in combination with one or more other drugs in the treatment, prevention, suppression or amelioration of diseases or conditions for which compounds of structural formula I or the other drugs have utility. Typically the combination of the drugs is safer or more effective than either drug alone, or the combination is safer or more effective than would be expected based on the additive properties of the individual drugs. Such other drug(s) may be administered, by a route and in an amount commonly used contemporaneously or sequentially with a compound of structural formula L When a compound of structural formula I is used contemporaneously with one or more other drugs, a combination product containing such other drug(s) and the compound of structural formula I is preferred. However, combination therapy also includes therapies in which the compound of structural formula I and one or more other drugs are administered on different overlapping schedules. It is contemplated that when used in combination with other active ingredients, the compound of the present invention or the other active ingredient or both may be used effectively in lower doses than when each is used alone. Accordingly, the pharmaceutical compositions of the present invention include those that contain one or more other active ingredients, in addition to a compound of structural formula I.

Examples of other active ingredients that may be administered in combination with a compound of structural formula I, and either administered separately or in the same pharmaceutical composition, include, but are not limited to:

(a) dipeptidyl peptidase IV (DP-IV) inhibitors;
(b) insulin sensitizing agents including (i) PPARγ agonists such as the glitazones (e.g. troglitazone, pioglitazone, englitazone, MCC-555, rosiglitazone, and the like) and other PPAR ligands, including PPARα/γ dual agonists, such as KRP-297, and PPARα agonists such as gemfibrozil, clofibrate, fenofibrate and bezafibrate, and (ii) biguanides, such as metformin and phenformin;

(c) insulin or insulin mimetics;

(d) sulfonylureas and other insulin secretagogues such as tolbutamide, glipizide, meglitinide and related materials;

(e) α-glucosidase inhibitors, such as acarbose;

(f) glucagon receptor antagonists such as those disclosed in WO 98/04528, WO 99/01423, WO 00/39088 and WO 00/69810;

(g) GLP-1, GLP-1 analogs, and GLP-1 receptor agonists such as those disclosed in WO00/42026 and WO00/59887;

(h) GIP, GIP mimetics such as those disclosed in WO00/58360, and GIP receptor agonists;

(i) PACAP, PACAP mimetics, and PACAP receptor 3 agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, rosuvastatin, and other statins), (ii) bile-acid sequestrants (cholestyramine, colestipol, and dialkylaminoalkyl derivatives of a cross-linked dextran), (iii) nicotinyl alcohol, nicotinic acid or a salt thereof, (iv) inhibitors of cholesterol absorption, such as ezetimibe and beta-sitosterol, (v) acyl CoA:cholesterol acyltransferase inhibitors, such as, for example, avasimibe, and (vi) anti-oxidants, such as probucol;

(k) PPARδ agonists, such as those disclosed in WO97/28149;

(l) antiobesity compounds such as fenfluramine, dexfenfluramine, phentermine, sibutramine, orlistat, neuropeptide $Y_1$ or $Y_5$ antagonists, CB1 receptor inverse agonists and antagonists, $β_3$ adrenergic receptor agonists, melanocortin-receptor agonists, in particular melanocortin-4 receptor agonists, ghrelin antagonists, and melanin-concentrating hormone (MCH) receptor antagonists;

(m) ileal bile acid transporter inhibitors;

(n) agents intended for use in inflammatory conditions other than glucocorticoids, such as aspirin, non-steroidal anti-inflammatory drugs, azulfidine, and selective cyclooxygenase-2 inhibitors;

(o) protein tyrosine phosphatase 1B (PTP-1B) inhibitors; and (p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan.

The above combinations include a compound of structural formula I, or a pharmaceutically acceptable salt or solvate thereof, with one or more other active compounds. Non-limiting examples include combinations of compounds of structural formula I with two or more active compounds selected from biguanides, sulfonylureas, HMG-CoA reductase inhibitors, PPAR agonists, PTP-1B inhibitors, DP-IV inhibitors, and anti-obesity compounds.

Any suitable route of administration may be employed for providing a mammal, especially a human, with an effective dose of a compound of the present invention. For example, oral, rectal, topical, parenteral, ocular, pulmonary, nasal and the like may be employed. Dosage forms include tablets, troches, dispersions, suspensions, solutions, capsules, creams, ointments, aerosols and the like. Preferably the compound of structural formula I is administered orally.

The effective dosage of the active ingredient varies depending on the particular compound employed, the mode of administration, the condition being treated and the severity of the condition. Such dosages may be ascertained readily by a person skilled in the art.

When treating or preventing the diseases and conditions described herein, for which compounds of structural formula I are indicated, satisfactory results are obtained when the compounds of the invention are administered at a daily dosage of from about 0.001 to about 100 milligram per kilogram (mpk) of body weight, preferably given as a single daily dose or in divided doses about two to four times a day. The total daily dosage thus ranges from about 0.1 mg to about 1000 mg, preferably from about 0.5 mg to about 100 mg. In the case of a typical 70 kg adult human, the total daily dose will range from as low as about 0.01 mg to as high as about 4000 mg. This dosage may be adjusted to provide the optimal therapeutic response.

Another aspect of the present invention relates to a pharmaceutical composition which comprises a compound of structural formula I, or a pharmaceutically acceptable salt or solvate thereof, in combination with a pharmaceutically acceptable carrier.

The compositions include compositions suitable for oral, rectal, topical, parenteral (including subcutaneous, intramuscular, and intravenous), ocular (ophthalmic), transdermal, pulmonary (nasal or buccal inhalation), or nasal administration, although the most suitable route in any given case will depend on the nature and severity of the condition being treated and the active ingredient. They may be conveniently presented in unit dosage form and prepared by any of the methods well-known in the art of pharmacy.

The compound of structural formula I can be combined with the pharmaceutical carrier according to conventional pharmaceutical compounding techniques. Carriers take a wide variety of forms. For example, carriers for oral liquid compositions include, e.g., water, glycols, oils, alcohols, flavoring agents, preservatives, coloring agents and other components used in the manufacture of oral liquid suspensions, elixirs and solutions. Carriers such as starches, sugars and microcrystalline cellulose, diluents, granulating agents, lubricants, binders, disintegrating agents and the like are used to prepare oral solid dosage forms, e.g., powders, hard and soft capsules and tablets. Solid oral preparations are preferred over oral liquids.

The oral solid dosage forms may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. Capsules may also contain a liquid carrier such as a fatty oil.

Various other materials may be present to act as coatings or to modify the physical form of the dosage unit. For instance, tablets may be coated with shellac, sugar or both.

Tablets may be coated by standard aqueous or nonaqueous techniques. The typical percentage of active compound in these compositions may, of course, be varied from about 2 percent to about 60 percent on a w/w basis. Thus, tablets contain a compound of structural formula I or a salt or hydrate thereof in an amount ranging from as low as about 0.1 mg to as high as about 1.5 g, preferably from as low as about 0.5 mg to as high as about 500 mg, and more preferably from as low as about 10 mg to as high as about 100 mg.

Oral liquids such as syrups or elixirs may contain, in addition to the active ingredient, sucrose as a sweetening agent, methyl and propylparabens as preservatives, a dye and a flavoring such as cherry or orange flavor.

Parenterals are typically in the form of a solution or suspension, typically prepared with water, and optionally including a surfactant such as hydroxypropylcellulose. Dispersions can be prepared in glycerol, liquid polyethylene glycols and mixtures thereof in oils. Typically preparations that are in diluted form also contain a preservative.

The pharmaceutical injectable dosage forms, including aqueous solutions and dispersions and powders for the extemporaneous preparation of injectable solutions or dispersions, are also sterile and must be fluid to the extent that easy syringability exists; they must be stable under the conditions of manufacture and storage and are usually preserved. The carrier thus includes the solvent or dispersion medium containing, for example, water, ethanol, polyol (e.g. glycerol, propylene glycol and liquid polyethylene glycol), suitable mixtures thereof, and vegetable oils.

Preparation of Compounds of the Invention:

The compounds of structural formula I of the present invention can be prepared according to the procedures of the following Schemes and Examples, using appropriate materials and are further exemplified by the following specific examples. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the their neutral form. All temperatures are degrees Celsius unless otherwise noted. Mass spectra (MS) were measured by electrospray ion-mass spectroscopy (ESMS).

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. Cbz and BOC are commonly used protecting groups in organic synthesis, and their removal conditions are known to those skilled in the art.

Abbreviations Used in the Description of the Preparation of the Compounds of the Present Invention:

| | |
|---|---|
| AIBN | 2,2'-azobisisobutyronitrile |
| BOC | t-butyloxycarbonyl |
| BBr$_3$ | boron tribromide |
| 9-BBN | 9-borabicyclo[3.3.1]nonane |
| Bn | benzyl |
| nBuLi | n-butyl lithium |
| Cbz | benzyloxycarbonyl |
| CDI | 1,1'-carbonyldiimidazole |
| MeOTf | methyl trifluoromethanesulfonate |
| CH$_2$Cl$_2$ | dichloromethane |
| CH$_2$I$_2$ | diiodomethane |
| (COCl)$_2$ | oxalyl chloride |
| Cs$_2$CO$_3$ | cesium carbonate |
| DAST | (diethylamino)sulfur trifluoride |
| DMAP | 4-(dimethylamino)pyridine |

| | |
|---|---|
| DMF | N,N-dimethylformamide |
| Et | ethyl |
| Et$_3$N | triethylamine |
| EtOAc | ethyl acetate |
| Et$_2$Zn | diethylzinc |
| H$_2$O$_2$ | hydrogen peroxide |
| Me | methyl |
| MeCN | acetonitrile |
| MeOH | methanol |
| mCPBA | meta-chloroperbenzoic acid |
| MS | mass spectrum |
| NaBH$_4$ | sodium borohydride |
| NaHCO$_3$ | sodium hydrogencarbonate |
| NaOAc | sodium acetate |
| NBS | N-bromosuccinimide |
| Ph | phenyl |
| PyBROP | bromotripyrrolidinophosphonium hexafluorophosphate |
| PPh$_3$ | triphenylphosphine |
| pyr | pyridine |
| SOCl$_2$ | thionyl chloride |
| TFA | trifluoroacetic acid |
| TFFH | N,N,N',N'-tetramethylformamidinium hexafluorophosphate |
| THF | tetrahydrofuran |
| TLC | thin-layer chromatography |
| TsOH | p-toluenesulfonic acid |

Reaction Schemes 1-3 illustrate the methods employed in the synthesis of the compounds of the present invention of structural formula I. All substituents are as defined above unless indicated otherwise.

Reaction Scheme 1 illustrates a key step in the synthesis of the novel compounds of structural formula I of the present invention. As shown in reaction Scheme 1, a sulfonobicyclo[2.2.2]carboxylic acid (1-A, where Y is a generic linker) can be coupled with Q which is a bicyclic or tricyclic amine to formamides of structural formula I. This coupling can be accomplished by first converting the carboxylic acid to an acid chloride (1-B), and then treating the acid chloride with the amine. This conversion of an acid to an acid chloride can commonly be accomplished using oxalyl chloride, phosphorous pentachloride, phosphorous oxychloride, thionyl chloride, or other reagents known to those skilled in the art. Alternatively, "standard peptide coupling reaction conditions" may be employed for making peptide bonds, for example PyBrop, PyBop, EDC, DCC, DIC as well as others known to those skilled in the art.

Alternatively, a sulfidobicyclo[2.2.2]carboxamide (2-A) can be oxidized to a sulfone as shown in reaction scheme 2. This oxidation can be accomplished using a variety of oxidizing reagents known to those skilled in the art, such as mCPBA or other peracids, oxone, or sodium hypochlorite.

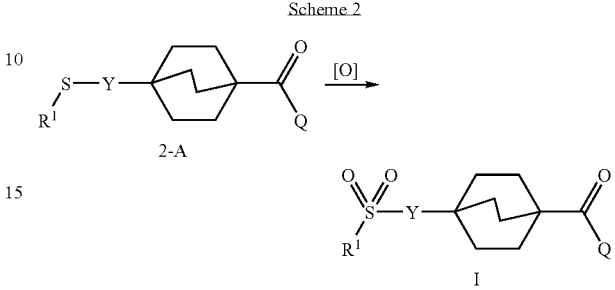

Alternatively, as shown in Scheme 3, a bicyclo[2.2.2]octanecarboxamide (3-A) bearing a leaving group (such as a chloride, bromide, iodide, mesylate, tosylate, or triflate, represented by X in the scheme) attached to the [2.2.2]bicycle can be reacted with a sulfinic acid to produce a sulfone by sulfur displacement of the leaving group.

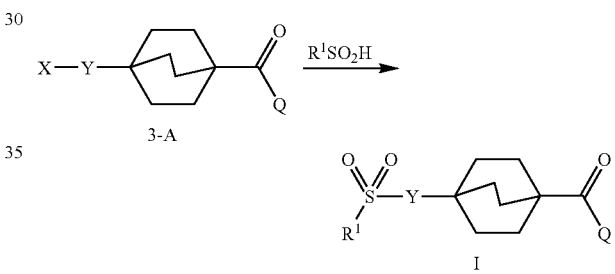

Alternatively, as shown in Scheme 4, in the case where "Y" is aryl, the aryl group may be sulfonated using sulfuric acid, "fuming" sulfuric acid, chlorosulfonic acid, or other sulfonating reagents known to those skilled in the art. The arylsulfonic acid can then be reduced to an arylsulfinic acid, commonly via the intermediate arylsulfonyl chloride. Commonly used

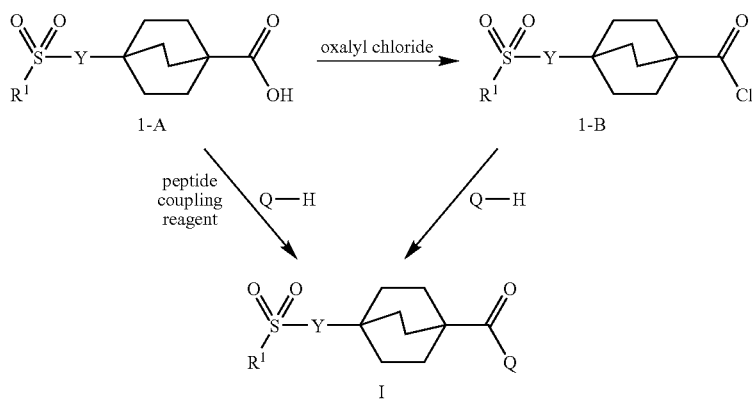

reagents for converting arylsulfonic acids to their chlorides include phosphorus pentachloride or thionyl chloride, and commonly used reagents for reducing arylsulfonyl chlorides to arylsulfinic acids include sodium sulfite or Zn and mild acid. The resulting arylsulfinic acid can then be alkylated on sulfur using a variety of carbon electrophiles including primary, secondary, allylic and benzylic chlorides, bromides, iodides, sulfates, mesylates, tosylates and triflates.

used to vary the length and character of the tether between the [2.2.2]bicyclooctyl nucleus and the sulfone function. An example of a general procedure is shown in intermediate scheme 4, where "Y" is a generic linker.

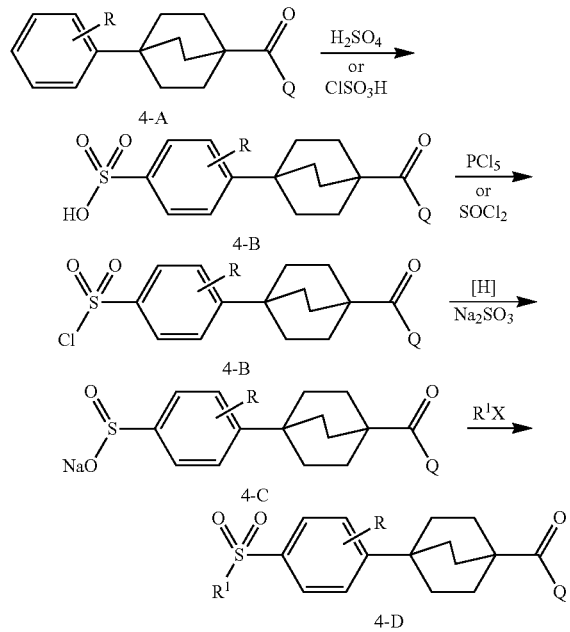

Scheme 4

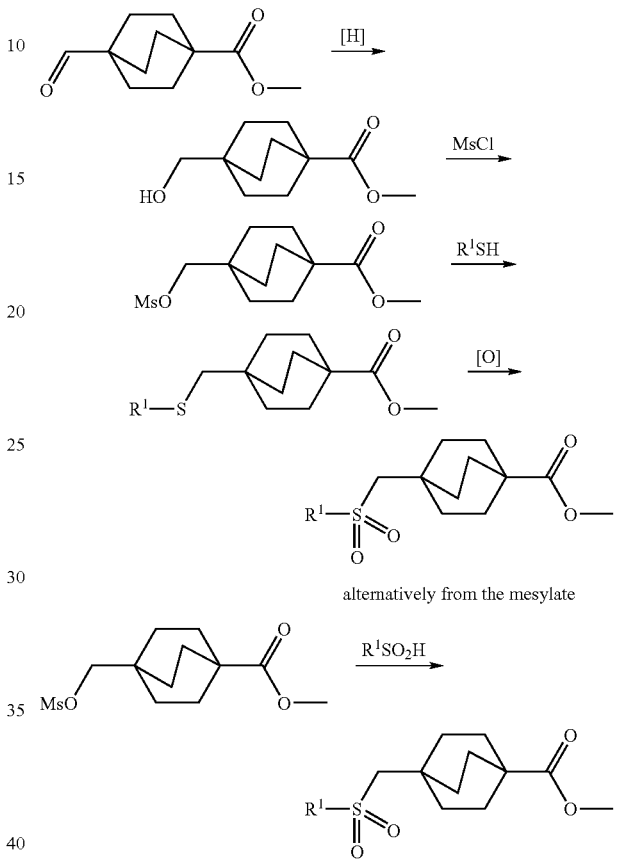

Intermediate Scheme 1

Alternatively, as shown in Scheme 5, in the case where "Y" is aryl, the aryl group may undergo an electrophilic sulfonylation reaction with an alkyl or aryl sulfonyl fluoride in the presence of a Lewis acid such as aluminum trichloride or boron tribromide.

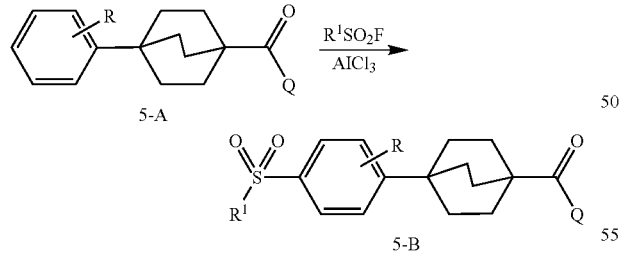

Scheme 5

Intermediate Schemes 1-10 describe the preparation of various

[2.2.2]bicyclooctylcarboxylic acids useful for the preparation of compounds of structure class I.

Intermediate Schemes 1-4 show methods for the synthesis of various mesylates, which can be displaced with thiols and then oxidized, or displaced directly with sulfinic acids (both techniques described above) to provide sulfonoester precursors to sulfonoamides. It will be understood by those skilled in the art that simple variations of these procedures can be

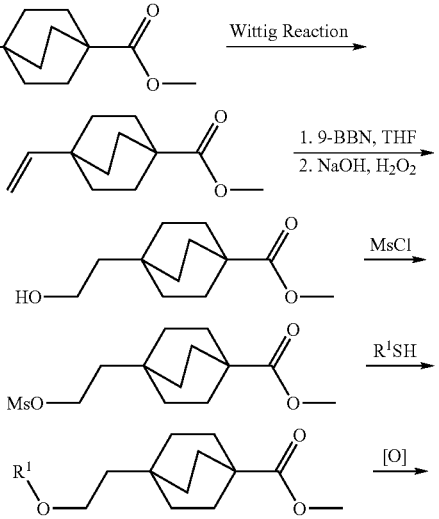

Intermediate Scheme 2

Intermediate Scheme 3

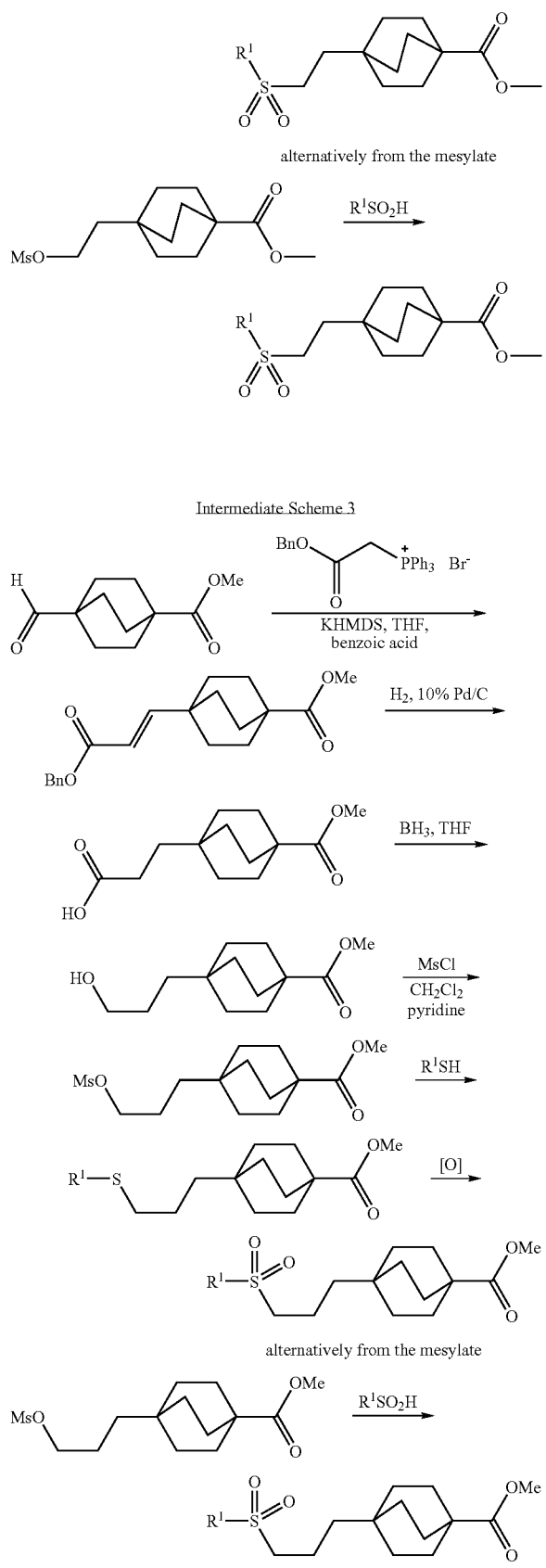

Intermediate Scheme 4

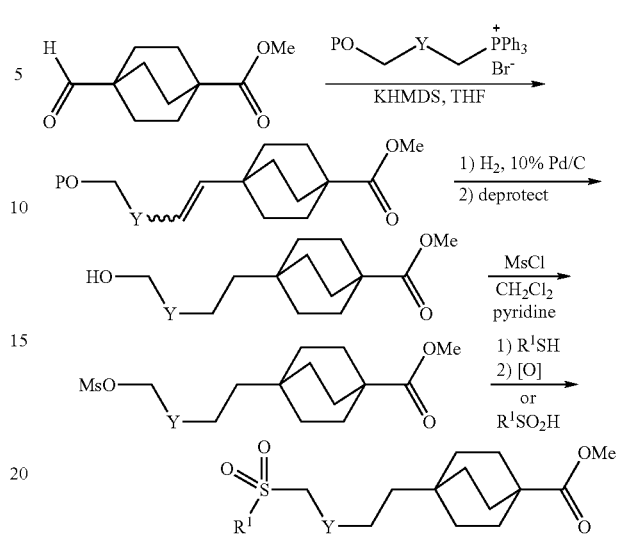

Alternatively, the mesylate can be displaced with a nucleophile, such as an alkoxide or thiolate, which is tethered to a sulfone function, as illustrated in Intermediate Schemes 5 & 6. In the general case shown in Intermediate Scheme 6, $Y^1$ and $Y^2$ represent generic linkers.

Intermediate Scheme 5

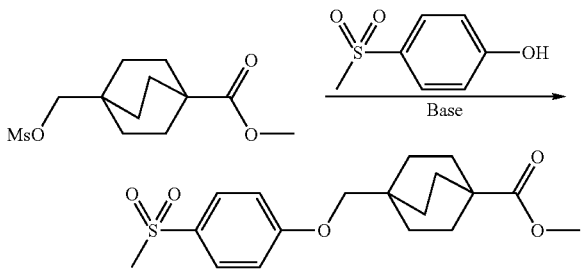

Intermediate Scheme 6

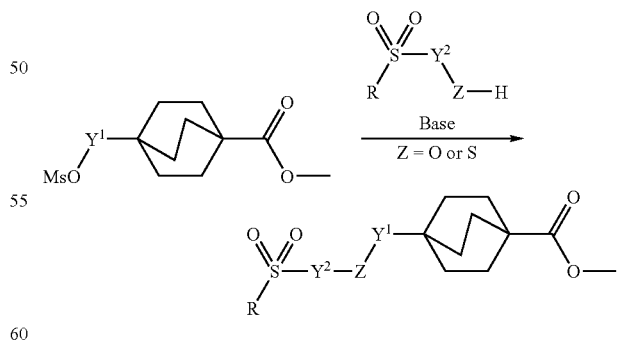

Intermediate Schemes 7 & 8 show methods for the direct introduction of the sulfone functionality via a Wittig or Wadsworth-Horner-Emmons reaction. It will be understood by those skilled in the art that simple variations of these procedures can be used to vary the length and character of the tether between the [2.2.2]bicyclooctyl nucleus and the sulfone function. An example of a general procedure is shown in intermediate scheme 6, where "Y" is a generic linker.

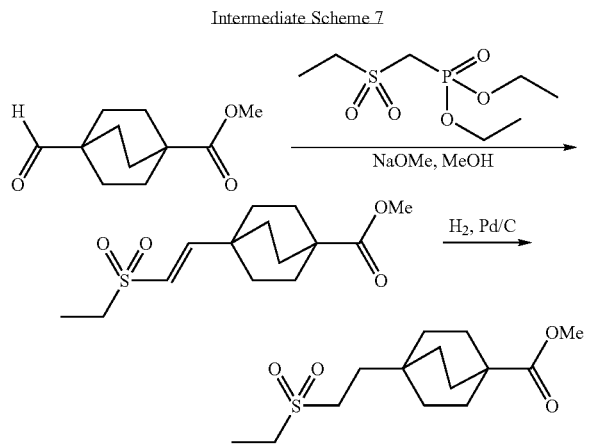

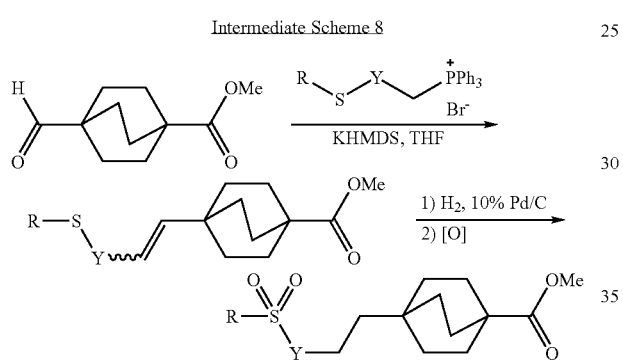

Intermediate Scheme 9 shows a method for the synthesis of aryl substituted [2.2.2]bicyclooctanecarboxylic acids, which can be electrophilically sulfonated or sulfonylated as described above.

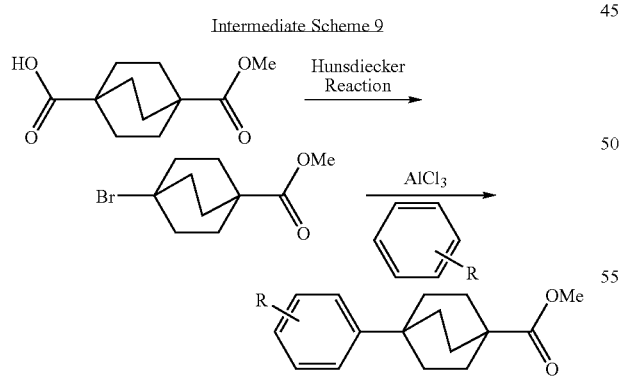

Intermediate Scheme 10 shows a method for the synthesis of sulfur substituted [2.2.2]bicyclooctanecarboxylic acids, which can be oxidized to produce structures in which the sulfone is attached directly to the bicyclic nucleus. Examples of sulfur nucleophiles which could be used here include sodium or potassium thiocyanate or thiourea. Deprotection of the first formed adduct can be accomplished hydrolytically to produce the thiol, which can then be alkylated with primary, secondary, allylic and benzylic halides and sulfonates. Alternatively, the bromide can be captured using a thiophenol to produce aryl [2.2.2]bicyclooctyl sulfides. In a final step, these sulfides can be oxidized to sulfones as described previously.

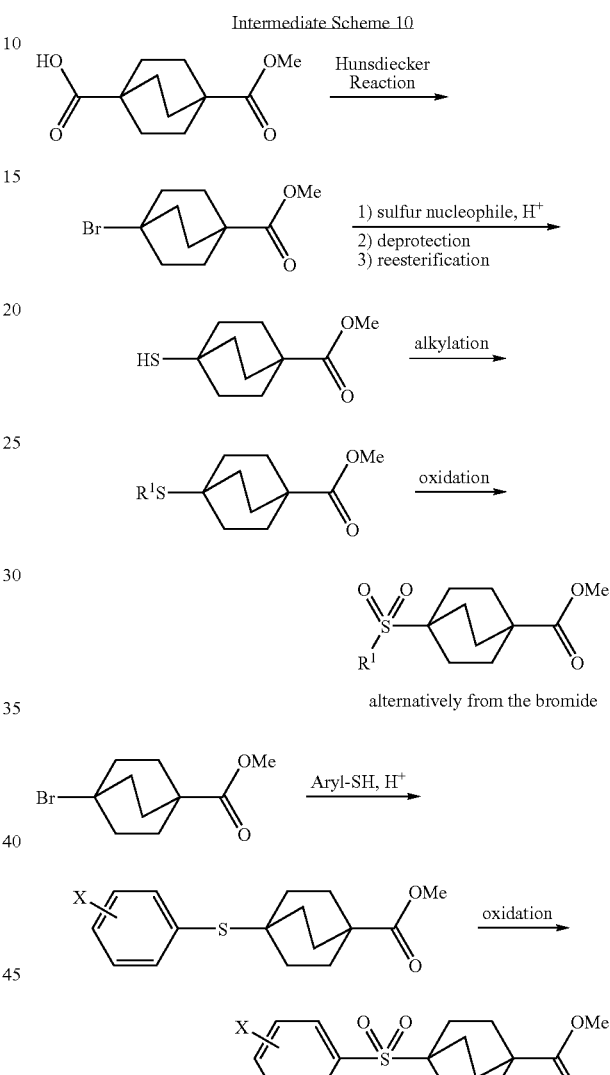

The following Examples are provided to illustrate the invention and are not to be construed as limiting the scope of the invention in any manner.

EXAMPLE 1

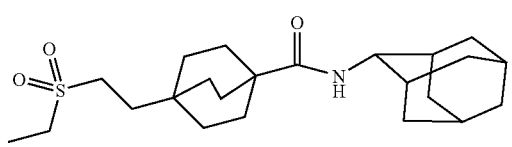

N-2-adamantyl-4-[2-(ethylsulfonyl)ethyl]bicyclo[2.2.2]octane-1-carboxamide (1-5)

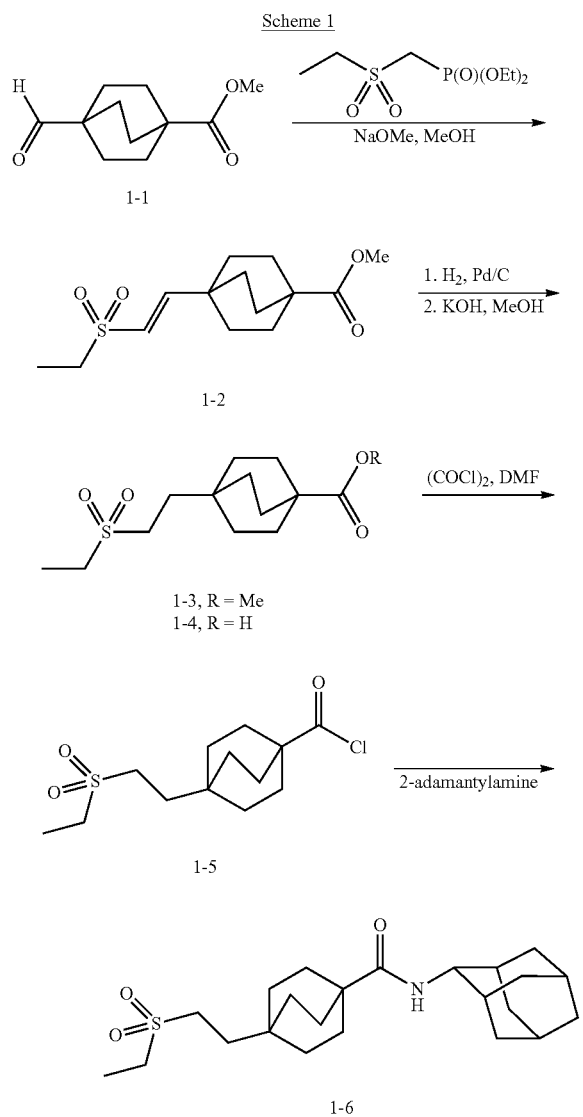

Step A:

Diethyl(ethylsulfonomethane)phosphonate (1.12 g, 4.6 mmol) (Popoff, I. C. et al. *J. Org. Chem.* 34: 1128-30 (1969)) and 4-carbomethoxybicyclo[2.2.2]octane-1-carboxaldehyde (1-1) (0.82 g, 4.2 mmol) (Adcock, W., Kok, G. B. *J. Org. Chem.* 50: 1079-1087 (1985)) were dissolved in 8 mL of absolute methanol. The mixture was placed under nitrogen atmosphere, cooled in an ice-bath, and treated with 0.5M solution of sodium methoxide in methanol (8.8 mL, 4.4 mmol). The reaction mixture was kept under reflux for 4 h, then cooled to room temperature, concentrated under diminished pressure, then treated with 2 mL of water and allowed to sit in the refrigerator overnight. The mixture was filtered and the solid washed with a small amount of cold 1:1 MeOH/water. The resulting white solid was collected and dried under vacuum to give the unsaturated sulfone 1-2. MS (ESI⁺)=287 (M+1).

Step B:

Sulfone 1-2 (880 mg, 3.08 mmol) was dissolved in a 1:2 mixture of ethyl acetate/methanol (30 mL), placed under nitrogen atmosphere, then treated with 10% Pd/C (800 mg). The reaction was placed under hydrogen atmosphere and stirred vigorously for 90 min. The resulting solution was filtered through celite, washed with methanol and ethyl acetate and evaporated to give methyl 4-[2-(ethylsulfonyl)ethyl]bicyclo[2.2.2]octane-1-carboxylate (1-3) as a white solid.

Step C:

Ester 1-3 (880 mg, 3 mmol) was dissolved in 10% water/methanol solution (100 mL) and treated with 1 g of potassium hydroxide. The reaction was heated at 60° C. for 1 h then at 45° C. overnight. The mixture was concentrated in vacuo then acidified to pH 2 with 1M HCl and extracted with three portions of methylene chloride. The organic layers were combined, dried over anhydrous sodium sulfate and evaporated to give 4-[2-(ethylsulfonyl)ethyl]bicyclo[2.2.2]octane-1-carboxylic acid (1-4) (810 mg).

Step D:

Carboxylic acid 1-4 (810 mg, 3 mmol) was dissolved in methylene chloride (5 ml) and treated with oxalyl chloride (4 eq.) and 0.050 ml of DMF. The reaction was stirred at room temperature for 45 min, then the solvent was removed under reduced pressure to give a quantitative crude yield of 4-[2-(ethylsulfonyl)ethyl]bicyclo[2.2.2]octane-1-carboxyl chloride (1-5).

Step E:

Amide 1-6 was made from acid chloride 1-5 (810 mg, 2.96 mmol) as one member of a 96 compound library, employing the technique of parallel synthesis using the Myriad Core System/nMiniblock. According to the general procedure, 0.10 mmol of each amine (2-adamantylamine for this product) was weighed into the miniblock reaction tubes, and 0.350 ml of dry DMF and 0.55 ml of dry diisopropylethylamine was added to each tube. A 0.25 M solution of the acid chloride in dry acetonitrile was prepared, and 0.400 ml of this solution was dispensed to each tube and the reactions were incubated and stirred overnight under an inert nitrogen atmosphere. The products were purified using a Fraction Lynx HPLC (with detection according to mass spectrum) equipped with a Waters Xterra MS C18 5 um 19×50 nm reverse phase column running a gradient of water/acetonitrile (0.1% TFA). The fractions containing product were concentrated to remove some of the acetonitrile and the lyophilized to provide pure product 4-[2-(ethylsulfonyl)ethyl]-N-methylbicyclo[2.2.2] octane-1-carboxamide 1-6 as a white fluffy amorphous solid.

MS (ESI⁺)=408 (M+1).

¹H NMR (500 MHz, CDCl₃): δ 5.90 (1H, d), 4.05 (1H, d), 3.04 (2H, q), 2.91 (2H, m), 1.94-1.66 (16H, multiplets), 1.83 (6H, distorted t), 1.49 (6H, distorted t), 1.44 (3H, triplet).

EXAMPLE 2

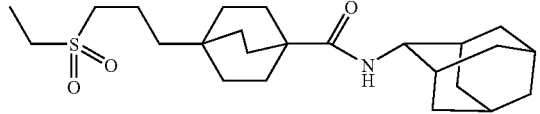

N-2-adamantyl-4-[3-(ethylsulfonyl)propyl]bicyclo[2.2.2]octane-1-carboxamide (2-9)

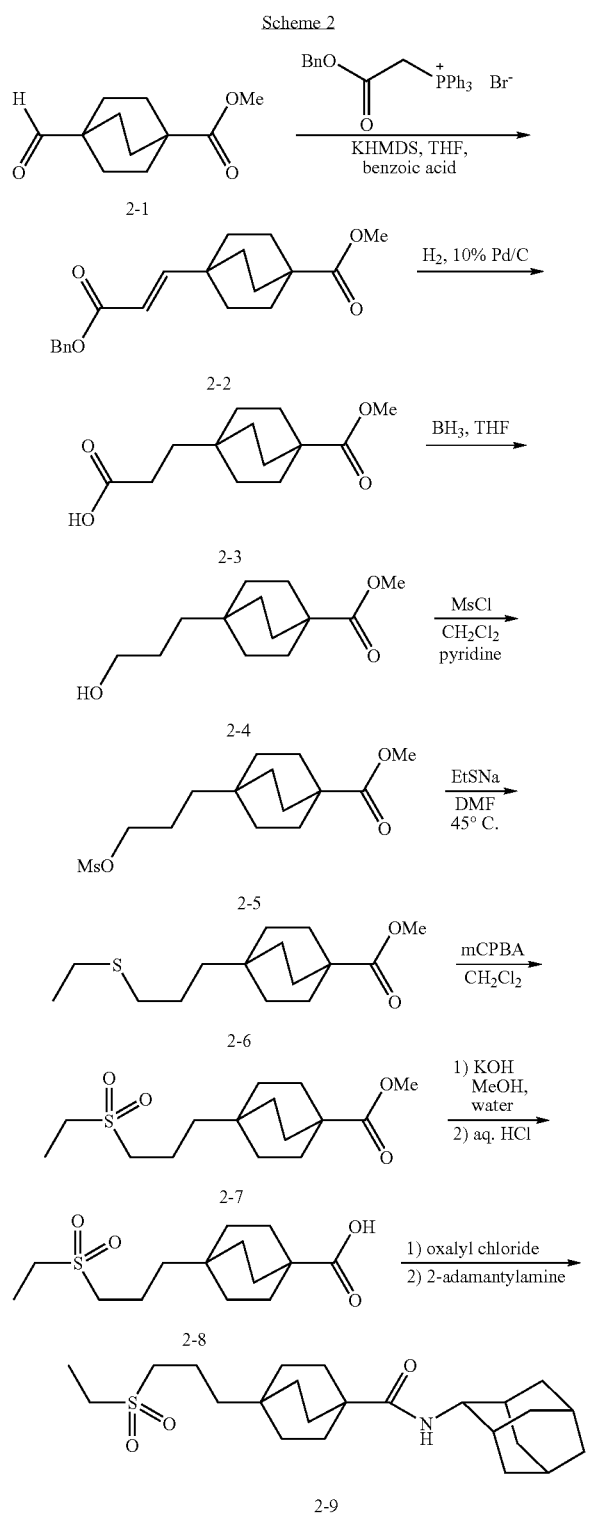

Step A:

(Benzyloxycarbonylmethyl)triphenylphosphonium bromide (4.6 g, 9.4 mmol) was azeotroped twice from toluene, and then suspended in 30 mL dry THF. Potassium hexamethyldisilazide (0.5 M in toluene, 16.8 mL, 8.4 mmol) was added dropwise at room temperature and the yellow solution was allowed to stir for 1 h, after which time it became milky white. A solution of 4-carbomethoxybicyclo[2.2.2]octane-1-carboxaldehyde (2-1) (0.50 g, 2.55 mmol) (Adcock, W., Kok, G. B. *J. Org. Chem.* 50: 1079-1087 (1985)) and benzoic acid (0.015 g, 0.13 mmol) in 2 mL of dry THF was prepared and added dropwise by syringe at room temperature. The mixture was heated to 90° C. and allowed to stir at reflux temperature, after which time the mixture was diluted with 200 mL of ethyl acetate and washed consecutively with 50 mL portions of 1 N HCl (twice), saturated aq. sodium bicarbonate, and brine. The organic layer was dried using magnesium sulfate, and the solvent was removed under reduced pressure. The residue was chromatographed on silica, eluting with a gradient of 5% to 10% ethyl acetate in hexane to provide methyl 4-[(1E)-3-(benzyloxy)-3-oxoprop-1-en-1-yl]bicyclo[2.2.2]octane-1-carboxylate (2-2) as a colorless oil. $^1$H NMR (500 MHz, CDCl$_3$): δ 7.4 (5H, m), 6.94 (1H, d, J=17 Hz), 5.77 (1H, d, J=17 Hz), 5.21 (2H, s), 3.69 (3H, s), 1.86 (6H, m), 1.63 (6H, m) ppm.

Step B:

Diester 2-2 (0.625 g, 1.90 mmol) was dissolved in a 1:1 mixture of ethyl acetate/methanol (30 mL), placed under nitrogen atmosphere, then treated with 10% Pd/C (500 mg) and 0.1 mL of acetic acid. The reaction was placed under hydrogen atmosphere and stirred vigorously for 2 hr. The resulting solution was filtered through celite and the solvent was removed under reduced pressure. The residue was partitioned between 200 mL of ethyl acetate and 200 mL of 1 N NaOH solution. The aqueous layer was separated and neutralized, then extracted three times with 50 mL of methylene chloride. The combined organic layers were dried over magnesium sulfate and the solvent was removed under reduced pressure to afford 3-[4-(methoxycarbonyl)bicyclo[2.2.2]oct-1-yl]propanoic acid (2-3). $^1$H NMR (500 MHz, CDCl$_3$): δ 3.62 (3H, s), 2.20 (2H, broad t, J=9 Hz), 1.75 (6H, m), 1.47 (2H, broad t, J=9 Hz), 1.38 (6H, m) ppm.

Step C:

Carboxylic acid 2-3 (400 mg, 1.67 mmol) was dissolved in tetrahydrofuran (5 mL) and borane (1 M solution in THF, 2.17 mL, 1.3 eq.) was added dropwise at room temperature. After 2 h the reaction was added to 50 mL of 1 N HCl and then extracted three times with 50 mL of methylene chloride. The combined organic layers were dried over magnesium sulfate and the solvent was removed under reduced pressure to afford crude methyl 4-(3-hydroxypropyl)bicyclo[2.2.2]octane-1-carboxylate (2-4) which was used without purification in the next step. $^1$H NMR (500 MHz, CD$_3$OD): δ 3.66 (3H, s), 3.62 (2H, t, J=6.5 Hz), 1.78 (6H, m), 1.50 (2H, m), 1.41 (2H, m), 1.17 (2H, m) ppm.

Step D:

Hydroxyester 2-4 (430 mg, 1.9 mmol) was dissolved in 2.5 mL of anhydrous methylene chloride under nitrogen atmosphere, treated with pyridine (0.5 mL) and methanesulfonyl chloride (0.368 mL, 4.8 mmol) and stirred for 4 h at room temperature. The mixture was diluted with 100 mL of ethyl acetate and washed with 1N aqueous HCl, saturated aqueous sodium bicarbonate, and brine. The organic layer was dried over anhydrous sodium sulfate and evaporated. The crude methyl 4-{3-[(methylsulfonyl)oxy]propyl}bicyclo-[2.2.2]octane-1-carboxylate (2-5) thus afforded was used without purification in the next reaction. $^1$H NMR (500 MHz, CDCl$_3$): δ 4.22 (2H, t, J=7.5 Hz), 3.68 (3H, s), 3.04 (3H, s), 1.82 (6H, m), 1.70 (2H, m), 1.44 (6H, m), 1.24 (2H, m) ppm.

Step E:

Mesylate 2-5 (3.30 g, 10.9 mmol) was dissolved in DMF (20 mL) and treated with sodium ethanethiolate (1.82 g, 21.7 mmol). The solution was stirred at 45° C. for 3 h, then the mixture was diluted with 100 mL of ethyl acetate and washed twice with 1N aqueous HCl, then with saturated aqueous sodium bicarbonate, and brine. The organic layer was dried over anhydrous sodium sulfate and evaporated to afford methyl 4-[3-(ethylthio)propyl]bicyclo[2.2.2]octane-1-carboxylate (2-6) as a crude oil which was used without purification in the next step.

$^1$H NMR (500 MHz, CDCl$_3$): δ 3.68 ppm (3H, s), 2.56 (2H, q, J=7 Hz), 2.51 (2H, t, J=7.5 Hz), 1.80 (6H, m), 1.52 (2H, m), 1.42 (6H, m), 1.28 (2H, t, J=7 Hz), 1.02 (2H, m).

Step F:

Sulfide 2-6 (3.0 g, 11 mmol) was dissolved in methylene chloride (50 mL) and treated with m-chloroperbenzoic acid (75%, 6.2 g). The solution was stirred at room temperature for 2 h, then the mixture was diluted with 100 mL of methylene chloride and washed with saturated aqueous sodium bicarbonate, then twice with saturated aqueous sodium bisulfite, then twice with saturated aqueous sodium bicarbonate, and brine. The organic layer was dried over anhydrous sodium sulfate and evaporated to afford methyl 4-[3-(ethylsulfonyl)propyl]bicyclo[2.2.2]octane-1-carboxylate (2-7) as a crude oil which was used without purification in the next step. $^1$H NMR (500 MHz, CDCl$_3$): δ 3.68 ppm (3H, s), 2.56 (2H, q, J=7 Hz), 2.51 (2H, t, J=7.5 Hz), 1.80 (6H, m), 1.52 (2H, m), 1.42 (6H, m), 1.28 (2H, t, J=7 Hz), 1.02 (2H, m) ppm.

Step G:

Sulfone 2-7 (3.1 g, 10 mmol) was dissolved in 9:1 MeOH/water (50 mL) and treated with potassium hydroxide (3 g). The solution was stirred at room temperature overnight, then the mixture was acidified with 1 N HCl and extracted four times with 50 mL of methylene chloride. The organic layer was dried over anhydrous sodium sulfate and evaporated to afford 4-[3-(ethylsulfonyl)propyl]bicyclo[2.2.2]octane-1-carboxylic acid (2-8) which was used without purification in the next step. $^1$H NMR (500 MHz, CDCl$_3$): δ 3.03 (2H, q, J=7 Hz), 2.94 (2H, dd, J=7.5 Hz), 1.84 (8H, m), 1.45 (8H, m), 1.30 (2H, m) ppm.

Step H:

Carboxylic acid 2-8 (0.100 g, 0.348 mmol) was dissolved in 2 mL of anhydrous methylene chloride under nitrogen atmosphere, treated with oxalyl chloride (2 M in methylene chloride, 2 eq., 0.348 mL, 0.696 mmol) and subsequently with 0.050 ml of DMF. The reaction was stirred at room temperature under nitrogen atmosphere for 90 min, then evaporated and placed under vacuum for 20 min. The acid chloride was dissolved in anhydrous methylene chloride (2 mL), and then treated with triethylamine (0.100 ml) and 2-adamantylamine (2 eq., 105 mg). The reaction stirred at ambient temperature for 1 hr. The mixture was diluted with 20 mL of methylene chloride and washed with 1N aqueous HCl, saturated aqueous sodium bicarbonate, and brine. The organic layer was dried over anhydrous sodium sulfate and evaporated. The product was purified using a Gilson HPLC with UV detection equipped with a C18 reverse phase column running a gradient of water/acetonitrile (0.1% TFA). The fractions containing product were concentrated to remove some of the acetonitrile and the lyophilized to provide pure product N-2-adamantyl-4-[3-(ethylsulfonyl)propyl]bicyclo[2.2.2]octane-1-carboxamide (2-9) as a white fluffy amorphous solid.

MS (ESI$^+$)=422 (M+1).

$^1$H NMR (500 MHz, CDCl$_3$): δ 5.90 (1H, d), 4.05 (1H, d), 3.03 (2H, q), 2.94 (2H, m), 1.94-1.66 (16H, multiplets), 1.82 (6H, distorted t), 1.48 (6H, distorted t), 1.45 (3H, triplet) 1.28 (2H, m).

EXAMPLE 3

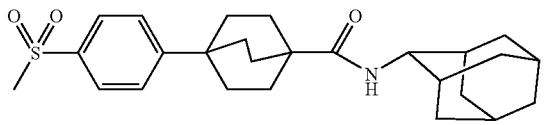

N-2-adamantyl-4-[4-(methylsulfonyl)phenyl]bicyclo[2.2.2]octane-1-carboxamide (3-4)

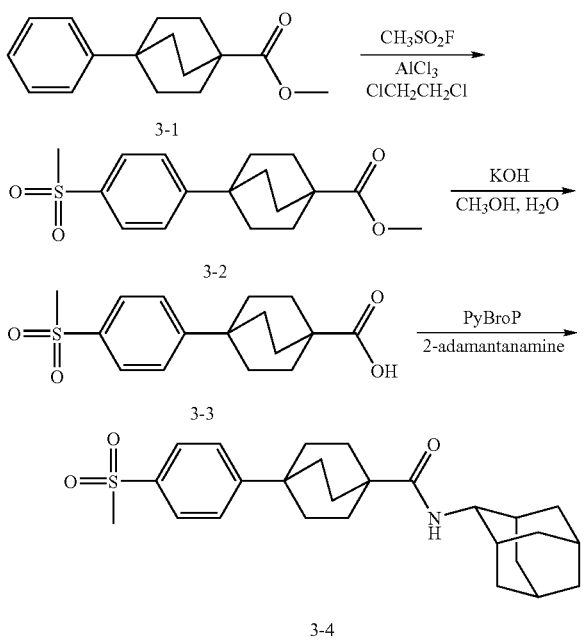

Step A:

To a stirred solution of methyl 4-phenylbicyclo[2.2.2]octane-1-carboxylate (3-1) (Chapman, N. B. et al. J. Org. Chem., 1970, 35, 917) (4.80 g, 19.6 mmol) in 1,2-dichloroethane (2 ml, 1M) was added methanesulfonyl fluoride (4.05 ml, 58.9 mmol) followed by aluminum trichloride (9.17 g, 68.8 mmol). The reaction mixture was stirred overnight under nitrogen atmosphere at ambient temperature followed by addition of another portion of methanesulfonyl fluoride (4.05 ml, 58.9 mmol) and aluminum trichloride (9.17 g, 68.8 mmol). The resulting mixture was heated at 80° C. for 3 h, then cooled to room temperature and diluted with 300 ml of dichloromethane and 200 ml water. The layers were separated and the aqueous layer was washed with two 100 ml portions of dichloromethane. The organic layers were combined, washed with brine, dried (MgSO$_4$), and concentrated in vacuo. The crude product was chromatographed on normal phase flash silica gel column, eluting with a gradient 10-50% EtOAc/hexanes to yield 1.4 g of 12-B (>95% pure). The material was recrystallized from EtOAc to yield sulfone 3-2.

$^1$H NMR (500 MHz, CDCl$_3$): δ 1.93 (6H, m), 1.99 (6H, m), 3.08 (3H, s), 3.73 (3H, s), 7.55 (2H, d, J=8.3 Hz), 7.90 (2H, d, J=8.1 Hz) ppm.

Step B:

Carboxylic acid 3-3 was prepared in quantitative yield by hydrolysis of ester 3-2 (1.1 g, 3.4 mmol) using the procedures described in Example 1, Step C. $^1$H NMR (500 MHz, CDCl$_3$): δ 1.98 (6H, m), 2.04 (6H, m), 3.11 (3H, s), 7.58 (2H, d, J=7.8 Hz), 7.92 (2H, d, J=7.9 Hz) ppm.

Step C:

Carboxylic acid 3-3 (0.060 g, 0.195 mmol) was dissolved in 0.500 mL of anhydrous methylene chloride under nitrogen atmosphere, treated with PyBroP (1 eq., 0.195 mmol, 0.076 g) and subsequently with DIEA (3 eq., 0.102 ml). The reaction was stirred at room temperature for 10 min, then treated with 2-adamantylamine (1 eq., 0.029 g). The reaction stirred at ambient temperature for 16 hr. The reaction was purified directly without workup using silica chromatography (Biotage Quad 3) eluting with 20% to 30% ethyl acetate in hexanes. The fractions containing product were concentrated to dryness, and the residue was lyophilized from benzene to provide pure product N-2-adamantyl-4-[4-(methylsulfonyl)phenyl]bicyclo[2.2.2]octane-1-carboxamide (3-4) as a white fluffy amorphous solid.

$^1$H NMR (500 MHz, CDCl$_3$): δ 7.89 (2H, d, J=8.5 Hz), 7.54 (2H, d, J=8.5 Hz), 5.94 (1H, d, J=8 Hz), 4.07 (1H, d, J=8 Hz), 1.96 (12H, broad s), 1.9-1.6 (14H, m).

MS (ESI$^+$)=442 (M+1).

EXAMPLE 4

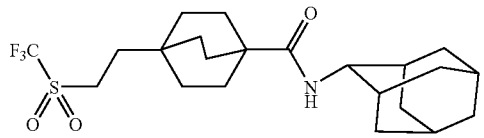

N-2-adamantyl-4-{2-[(trifluoromethyl)sulfonyl]ethyl}bicyclo[2.2.2]octane-1-carboxamide (4-6)

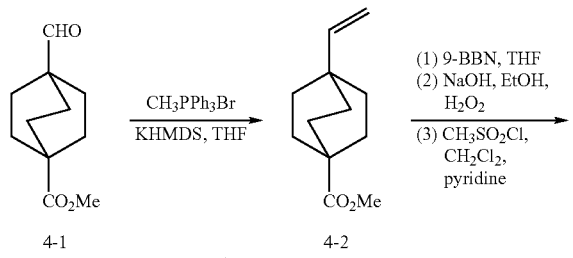

4-3: R = H
4-4: R = SO$_2$CH$_3$

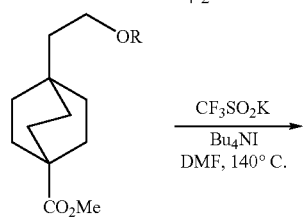

4-5

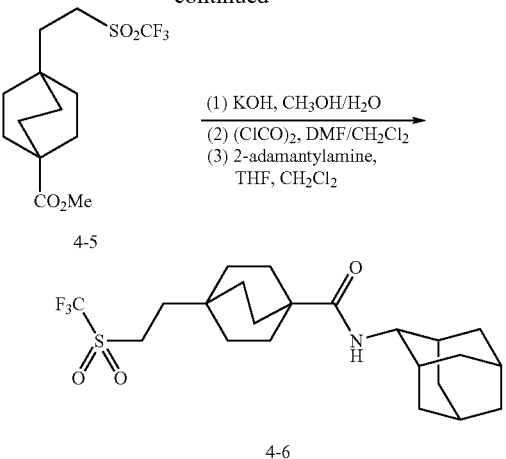

4-6

Step A:

To a stirred solution of methyltriphenylphosphonium bromide (9.1 g, 12.8 mmol) in THF (50 ml) at 0° C. was added potassium hexamethyldisilazide (0.5M in toluene, 48.6 ml), dropwise over 5 min. The resulting mixture was allowed to warm up to room temperature over 1 h, then cooled again to 0° C. and treated with methyl 4-formylbicyclo[2.2.2]octane-1-carboxylate (4-1) (Chapman, N. B. et al. J. Org. Chem., 1970, 35, 917) (2.5 g, 12.8 mmol). The reaction mixture was stirred at room temperature for 18 h then diluted with EtOAc (350 ml). The organic phase was washed with aqueous HCl (1 N), saturated aqueous sodium bicarbonate, and brine, then dried (Na$_2$SO$_4$) and concentrated in vacuo. The resulting solid was purified by flash silica gel chromatography, eluting with a gradient 0-4% EtOAc/hexanes. The resulting methyl 4-vinylbicyclo[2.2.2]octane-1-carboxylate (4-2) was isolated as a clear, colorless oil.

Step B:

To a stirred solution of olefin 4-2 (1.6 g, 8.3 mmol) in THF (20 ml) was added 9-BBN (0.5M in THF, 49 ml), dropwise. The solution was allowed to stir at room temperature for 18 h, then treated sequentially with ethanol (14.5 ml), aqueous NaOH (5N, 5 ml), and hydrogen peroxide (30% aqueous, 9.7 ml). The reaction mixture was acidified to pH=2 with aqueous HCl (1 N) and extracted three times with CH$_2$Cl$_2$. The organic layers were combined, washed with brine, dried (Na$_2$SO$_4$), and stripped. The resulting alcohol 4-3 was purified by silica gel chromatography eluting with a gradient 30-50% EtOAc/hexanes and isolated as a clear, colorless oil.

Step C:

A solution of alcohol 4-3 (1.5 g, 7.1 mmol) in CH$_2$Cl$_2$ (7.5 ml), pyridine (1.5 ml) was cooled to 0° C. and treated with methanesulfonyl chloride (1.65 ml, 21.3 mmol), dropwise over 5 min. The reaction mixture was allowed to warm to room temperature, then stirred for 3 h. EtOAc (300 ml) was added and the organic phase was washed with aqueous HCl (1 N) three times, saturated aqueous sodium bicarbonate two times, and brine. The organic layer was dried (Na$_2$SO$_4$), and stripped to yield methyl 4-{2-[(methylsulfonyl)oxy]ethyl}bicyclo[2.2.2]octane-1-carboxylate (4-4) as a white solid.

$^1$H NMR (500 MHz, CDCl$_3$): δ 1.52 (6H, m), 1.66 (2H, t, J=7.1 Hz), 1.84 (6H, m), 3.04 (3H, s), 3.69 (3H, s), 4.29 (2H, t, J=7.2 Hz) ppm.

Step D:

A solution of mesylate 4-4 (0.25 g, 0.86 mmol), potassium trifluoromethanesulfinate (0.3 g, 1.72 mmol), and tetrabutylammonium iodide (0.15 g, 0.4 mmol) in DMF (5 ml) was heated at 140° C. for 5 h. under nitrogen atmosphere. The solution was then cooled to room temperature and diluted with EtOAc (100 ml) and washed with aqueous HCl (1N) two times and brine. The organic layer was dried (Na₂SO₄), stripped, and chromatographed on flash silica gel, eluting with a gradient 5-20% EtOAc/hexanes. The resulting trifluoromethylsulfone (4-5) was isolated as a white solid.

¹H NMR (500 MHz, CDCl₃): δ 1.50 (6H, m), 1.78 (2H, m), 1.82 (6H, m), 3.17 (2H, m), 3.67 (3H, s) ppm.

Step E:

Sulfone ester 4-5 (45 mg, 0.14 mmol) was dissolved in 9:1 MeOH/water (1 mL) and treated with potassium hydroxide (0.1 g). The solution was stirred at room temperature overnight, then the mixture was acidified with 1 N HCl and extracted four times with 50 mL of methylene chloride. The organic layer was dried over anhydrous sodium sulfate and evaporated to afford 4-{2-[(trifluoromethyl)sulfonyl]ethyl}bicyclo[2.2.2]octane-1-carboxylic acid which was used without purification. The crude carboxylic acid was dissolved in 2 mL of anhydrous methylene chloride under nitrogen atmosphere, treated with oxalyl chloride (2 M in methylene chloride, 2 eq., 0.14 mL, 0.28 mmol) and subsequently with 0.010 ml of DMF. The reaction was stirred at room temperature under nitrogen atmosphere for 90 min, then evaporated and placed under vacuum for 20 min. The acid chloride was dissolved in anhydrous methylene chloride (1 mL), and then treated with triethylamine (0.050 ml) and 2-adamantylamine (2 eq., 0.28 mmol). The reaction stirred at ambient temperature for 1 hr. The mixture was diluted with 20 mL of methylene chloride and washed with 1N aqueous HCl, saturated aqueous sodium bicarbonate, and brine. The organic layer was dried over anhydrous sodium sulfate and evaporated. The product was purified using a Gilson HPLC with UV detection equipped with a C18 reverse phase column running a gradient of water/acetonitrile (0.1% TFA). The fractions containing product were concentrated to remove some of the acetonitrile and the lyophilized to provide pure product N-2-adamantyl-4-{2-[(trifluoromethyl)sulfonyl]ethyl}bicyclo[2.2.2]octane-1-carboxamide (4-6) as a white fluffy amorphous solid.

MS (ESI⁺)=448 (M+1).

¹H NMR (500 MHz, CDCl₃): δ 5.88 (1H, d), 4.03 (1H, d), 3.16 (2H, m), 1.95-1.65 (16H, multiplets), 1.85 (6H, distorted triplet), 1.50 (6H, distorted triplet).

EXAMPLE 5

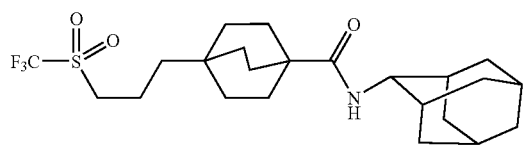

N-2-adamantyl-4-{3-[(trifluoromethyl)sulfonyl]propyl}bicyclo[2.2.2]octane-1-carboxamide (5-2)

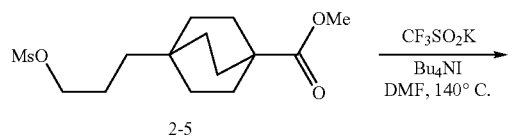

2-5

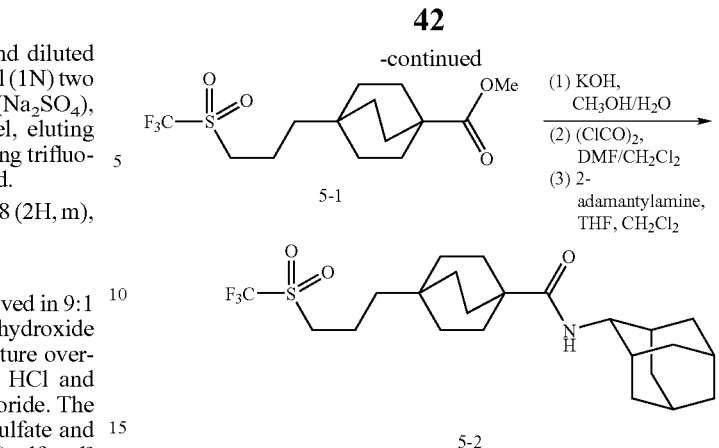

5-1

5-2

Step A:

A solution of mesylate 2-5 (0.305 g, 1.00 mmol, prepared as described in example 2), potassium trifluoromethanesulfinate (2 eq., 0.343 g, 2.0 mmol), and tetrabutylammonium iodide (0.5 eq., 0.184 g, 0.50 mmol) in DMF (5 ml) was heated at 135° C. for 5 h under nitrogen atmosphere. The solution was then cooled to room temperature and diluted with EtOAc (50 ml) and washed with aqueous HCl (1N) two times and brine. The organic layer was dried (Na₂SO₄), stripped, and chromatographed on flash silica gel, eluting with a gradient 5-20% EtOAc/hexanes. The resulting trifluoromethylsulfone (5-1) was isolated as a white solid.

Step B:

Sulfone ester 5-1 (164 mg, 0.48 mmol) was dissolved in 9:1 MeOH/water (3 mL) and treated with potassium hydroxide (0.5 g). The solution was stirred at room temperature overnight, then the mixture was acidified with 1 N HCl and extracted four times with 50 mL of methylene chloride. The organic layer was dried over anhydrous sodium sulfate and evaporated to afford 4-{2-[(trifluoromethyl)sulfonyl]ethyl}bicyclo[2.2.2]octane-1-carboxylic acid in crude quantitative yield.

Crude carboxylic acid (0.100 g, 0.300 mmol) was dissolved in 2 mL of anhydrous methylene chloride under nitrogen atmosphere, treated with oxalyl chloride (2 M in methylene chloride, 2 eq., 0.30 ml) and subsequently with 0.010 ml of DMF. The reaction was stirred at room temperature under nitrogen atmosphere for 90 min, then evaporated and placed under vacuum for 20 min. The acid chloride was dissolved in anhydrous methylene chloride (1 mL), and then treated with triethylamine (0.050 ml) and 2-adamantylamine (2 eq., 0.60 mmol). The reaction stirred at ambient temperature for 1 hr. The mixture was diluted with 20 mL of methylene chloride and washed with 1N aqueous HCl, saturated aqueous sodium bicarbonate, and brine. The organic layer was dried over anhydrous sodium sulfate and evaporated. The product was purified using a Gilson HPLC with UV detection equipped with a C18 reverse phase column running a gradient of water/acetonitrile (0.1% TFA). The fractions containing product were concentrated to remove some of the acetonitrile and the lyophilized to provide pure product N-2-adamantyl-4-{3-[(trifluoromethyl)sulfonyl]propyl}bicyclo[2.2.2]octane-1-carboxamide (5-2) as a white fluffy amorphous solid.

MS (ESI⁺)=462 (M+1).

¹H NMR (500 MHz, CDCl₃): δ 5.90 (1H, d), 4.05 (1H, d), 3.21 (2H, t), 1.95-1.65 (16H, multiplets), 1.82 (6H, distorted triplet), 1.49 (6H, distorted triplet), 1.34 (2H, m Hz).

EXAMPLES 6-19

Following procedures similar to those described above, the following compounds of formula II were also prepared:

Table (continued)

Structure I:

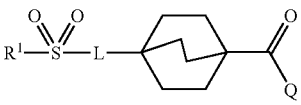

| Ex. # | R¹ | L | Q | Parent Ion m/z |
|---|---|---|---|---|
| 6 | ethyl | ethylene | 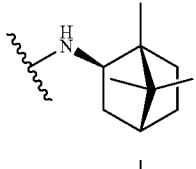 | 338 |
| 7 | ethyl | ethylene | 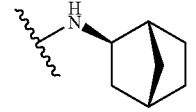 | 406 |
| 8 | ethyl | ethylene | 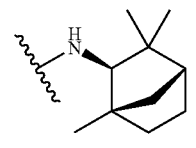 | 352 |
| 9 | ethyl | ethylene | 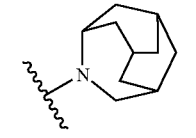 | 372 |
| 10 | ethyl | ethylene | 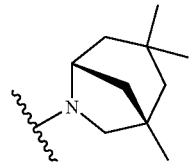 | 356 |
| 11 | ethyl | ethylene | 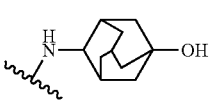 | 368 |
| 12 | ethyl | ethylene | 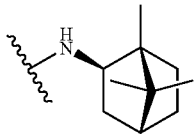 | 424 |
| 13 | ethyl | propylene | 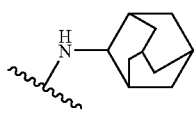 | 384 |
| 14 | ethyl | methylene | 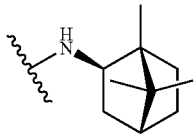 | 383 |
| 15 | ethyl | methylene | 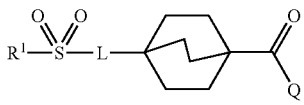 | 416 |
| 16 | ethyl | methylene | 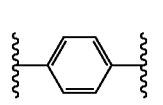 | 422 |
| 17 | methyl | 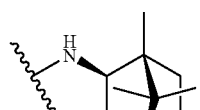 | 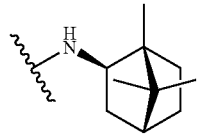 | 354 |
| 18 | CF₃ | ethylene | 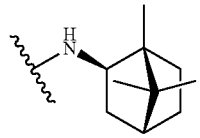 | 382 |
| 19 | CF₃ | propylene | 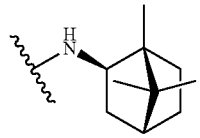 | 422 |

EXAMPLE OF A PHARMACEUTICAL FORMULATION

A specific embodiment of an oral composition within the present invention is an oral capsule, prepared by combining 50 mg of a compound described in one of the Examples with sufficient lactose to provide a total amount of 580 to 590 mg to fill a size 0 hard gelatin capsule.

Assays: Measurement of Inhibition Constants:

In vitro enzymatic activity was assessed for test compounds via a Scintillation Proximity Assay (SPA). In short, tritiated-cortisone substrate, NADPH cofactor and titrated compound of structural formula I were incubated with 11β-HSD1 enzyme at 37° C. to allow conversion to cortisol to progress. Following this incubation, a preparation of protein A coated SPA beads, pre-blended with anti-cortisol monoclonal antibody and a non-specific 11β-HSD inhibitor, such as 18β-glycyrrhetinic acid, was added to each well. The mixture was shaken at 15° C. and was then read on a liquid scintillation counter suitable for 96 well plates. Percent inhibition was calculated relative to a non-inhibited control well and IC$_{50}$ curves were generated. This assay was similarly applied to 11β-HSD2, whereby tritiated cortisol and NAD were used as the substrate and cofactor, respectively. To begin the assay, 40 μL of substrate (25 nM ³H-Cortisone+1.25 mM NADPH in 50 mM HEPES Buffer, pH 7.4) was added to designated wells on a 96-well plate. The compound was dissolved in DMSO at 10 mM followed by a subsequent 50 fold dilution in DMSO. The diluted material was then titrated 4 fold, seven times. 1 μL of each titrated compound was then added in duplicate to the substrate. To start the reaction, 10 μL of 11β-HSD1 microsome from CHO transfectants was added to each well at the appropriate concentration to yield approximately 10% conversion of the starting material. For ultimate calculation of percent inhibition, a series of wells were added that represented the assay minimum and maximum: one set that contained substrate without compound or enzyme (background), and another set that contained substrate and enzyme without any compound (maximum signal). The plates were spun briefly at a low speed in a centrifuge to pool the reagents, sealed with an adhesive strip, mixed gently, and incubated at 37° C. for 2 h. After incubation, 45 μL of SPA beads, presuspended with anti-cortisol monoclonal antibody and a compound of formula I, were added to each well. The plates were resealed and shaken gently for greater than 1.5 h at 15° C. Data were collected on a plate based liquid scintillation counter such as a Topcount. To control for inhibition of anti-cortisol antibody/cortisol binding, substrate spiked with 1.25 nM $^3$H cortisol was added to designated single wells. 1 μL of 200 μM compound was added to each of these wells, along with 10 μL of buffer instead of enzyme. Any calculated inhibition was due to compound interfering with the cortisol binding to the antibody on the SPA beads.

Assays: Measurement of In Vivo Inhibition:

In general terms, the test compound was dosed orally to a mammal and a prescribed time interval was allowed to elapse, usually between 1 and 24 h. Tritiated cortisone was injected intravenously, followed several min later by blood collection. Steroids were extracted from the separated serum and analyzed by HPLC. The relative levels of $^3$H-cortisone and its reduction product, $^3$H-cortisol, were determined for the compound and vehicle-dosed control groups. The absolute conversion, as well as the percentage of inhibition, was calculated from these values.

More specifically, compounds were prepared for oral dosing by dissolving them in vehicle (5% hydroxypropyl-beta-cyclodextrin v/v H$_2$O, or equivalent) at the desired concentration to allow dosing at typically 10 mg per kg. Following an overnight fasting, the solutions were dosed to ICR mice (obtained from Charles River) by oral gavage, 0.5 mL per dose per animal, with three animals per test group.

After the desired time had passed, routinely either 4 or 16 h, 0.2 mL of 3 μM $^3$H-cortisone in dPBS was injected by tail vein. The animal was caged for two min followed by euthanasia in a CO$_2$ chamber. Upon expiration, the mouse was removed and blood was collected by cardiac puncture. The blood was set aside in a serum separation tube for no less than 30 min at room temperature to allow for adequate coagulation. After the incubation period, blood was separated into serum by centrifugation at 3000×g, 4° C., for 10 min.

To analyze the steroids in the serum, they were first extracted with organic solvent. A 0.2 mL volume of serum was transferred to a clean microcentrifuge tube. To this a 1.0 mL volume of ethyl acetate was added, followed by vigorous vortexing for 1 min. A quick spin on a microcentrifuge pelleted the aqueous serum proteins and clarified the organic supernatant. 0.85 mL of the upper organic phase was transferred to a fresh microcentrifuge tube and dried. The dried sample was resuspended in 0.250 mL of DMSO containing a high concentration of cortisone and cortisol for analysis by HPLC.

A 0.200 mL sample was injected onto a Metachem Inertsil C-18 chromatography column equilibrated in 30% methanol. A slow linear gradient to 50% methanol separated the target steroids; simultaneous monitoring by UV at 254 nm of the cold standards in the resuspension solution acted as an internal standard. The tritium signal was collected by a radiochromatography detector that uploaded data to software for analysis. The percent conversion of $^3$H-cortisone to $^3$H-cortisol was calculated as the ratio of AUC for cortisol over the combined AUC for cortisone and cortisol.

While the invention has been described and illustrated in reference to specific embodiments thereof, those skilled in the art will appreciate that various changes, modifications, and substitutions can be made therein without departing from the spirit and scope of the invention. For example, effective dosages other than the preferred doses as set forth hereinabove may be applicable as a consequence of variations in the responsiveness of the human being treated for a particular condition. Likewise, the pharmacologic response observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended therefore that the invention be limited only by the scope of the claims which follow and that such claims be interpreted as broadly as is reasonable.

What is claimed is:

1. A compound represented by structural formula I

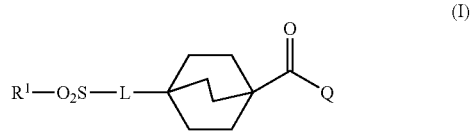

or a pharmaceutically acceptable salt thereof; wherein:

Q represents NR$^2$R$^3$ or a group selected from the following:

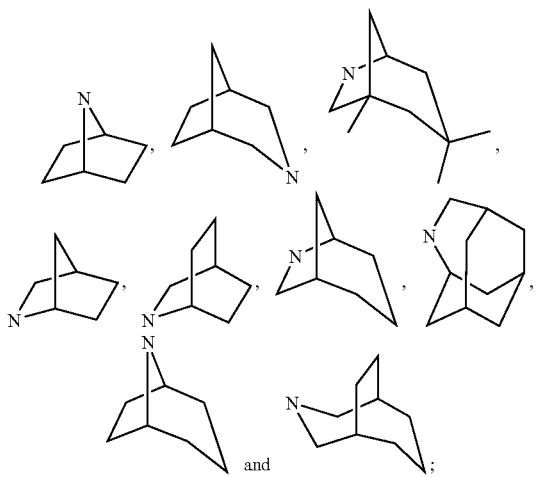

wherein said group may be optionally substituted with from one to five substituents selected from the group consisting of halo, C$_{1-3}$alkyl, C$_{1-3}$alkoxy, C$_{1-3}$haloalkyl and hydroxyl;

L represents the linking group —(CH$_2$)$_a$—X—(CH$_2$)$_b$—, wherein:

X represents a bond or is selected from the group consisting of: O, S, NH, N(C$_{1-3}$alkyl), C(O)NH, NHC(O), vinyl, Aryl, Aryloxy and HAR, when L is other than a bond, said group L is optionally substituted with 1-5 groups selected from: halo, cyano, C$_{1-4}$alkoxy, C$_{1-4}$alkylthio, hydroxy and amino;

said Aryl, Aryloxy and HAR groups being optionally substituted with 1-5 groups selected from halo, cyano, $C_{1-4}$alkoxy, $C_{1-4}$alkylthio, hydroxy and amino;

when X is O, S, NH or N($C_{1-3}$alkyl), a represents an integer of from 2-6 and b represents an integer of from 0-4, such that the sum of a and b is from 2-6;

and when X is a bond, C(O)NH, NHC(O), vinyl, Aryl, Aryloxy or HAR, a and b each represent integers of from 0-6, such that the sum of a and b is 0 to 6;

$R^1$ selected from the group consisting of: $C_{1-6}$alkyl, $C_{2-6}$alkenyl, Aryl or HAR, optionally substituted with one to five of the following groups: halo, cyano, $C_{1-4}$alkoxy, $C_{1-4}$alkylthio, hydroxy, amino, Aryl and HAR, said Aryl and HAR being further optionally substituted with one to three substituents independently selected from cyano, halo, hydroxy, amino, carboxy, trifluoromethyl, trifluoromethoxy, $C_{1-4}$alkyl, and $C_{1-4}$alkoxy;

$R^2$ is H or $C_{1-3}$alkyl; and

R3 is a bicyclic or tricyclic alkyl moiety having 6-12 carbon atoms, optionally substituted with 1-4 substituents selected from the group consisting of $C_{1-4}$alkyl, halo, halo$C_{1-4}$ alkyl, $C_{1-4}$alkoxy, halo$C_{1-4}$alkoxy, OH, $C_{1-6}$alkyl-$SO_2$— and phenyl-$SO_2$—, the alkyl and phenyl portions of $C_{1-6}$alkyl-$SO_2$— and phenyl-$SO_2$— being optionally substituted with 1-3 halo, $C_{1-3}$alkyl, halo$C_{1-3}$ alkyl, $C_{1-3}$alkoxy and halo$C_{1-3}$alkoxy groups.

2. A compound of formula I:

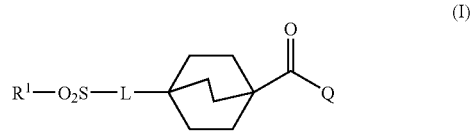

(I)

or a pharmaceutically acceptable salt thereof; wherein:

Q represents $NR^2R^3$ or a group selected from the following:

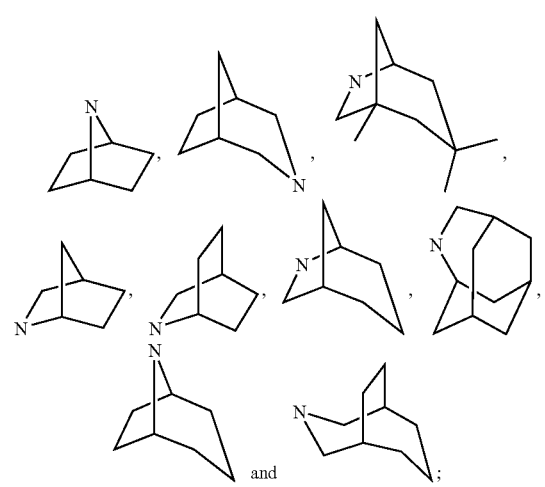

wherein said group may be optionally substituted with from one to five substituents selected from the group consisting of halo, $C_{1-3}$alkyl, $C_{1-3}$alkoxy, $C_{1-3}$haloalkyl and hydroxyl;

L represents the linking group —$(CH_2)_a$—X—$(CH_2)_b$—, wherein:

X represents a bond or is selected from the group consisting of: O, S, NH, N($C_{1-3}$alkyl), C(O)NH, NHC(O), vinyl, Aryl, Aryloxy and HAR, when L is other than a bond, said group L is optionally substituted with 1-5 groups selected from: halo, cyano, $C_{1-4}$alkoxy, $C_{1-4}$alkylthio, hydroxy and amino;

said Aryl, Aryloxy and HAR groups being further optionally substituted with one to five of the following groups: halo, cyano, $C_{1-4}$alkoxy, $C_{1-4}$alkylthio, hydroxy and amino;

when X is O, S, NH or N($C_{1-3}$alkyl), a represents an integer of from 2-6 and b represents an integer of from 0-4, such that the sum of a and b is from 2-6;

and when X is a bond, C(O)NH, NHC(O), vinyl, Aryl, Aryloxy or HAR, a and b each represent integers of from 0-6, such that the sum of a and b is 0 to 6;

$R^1$ represents a member selected from the group consisting of: $C_{1-6}$alkyl or $C_{2-6}$alkenyl, optionally substituted with one to five of the following groups: halo, cyano, $C_{1-4}$alkoxy, $C_{1-4}$alkylthio, hydroxy, amino, Aryl and HAR, said Aryl and HAR being further optionally substituted with one to three substituents independently selected from cyano, halo, hydroxy, amino, carboxy, trifluoromethyl, trifluoromethoxy, $C_{1-4}$alkyl, and $C_{1-4}$alkoxy;

$R^2$ is H or $C_{1-3}$alkyl; and $R^3$ is a bicyclic or tricyclic alkyl moiety having 6-12 carbon atoms, optionally substituted with 1-4 substituents selected from the group consisting of $C_{1-4}$alkyl, halo, halo$C_{1-4}$ alkyl, $C_{1-4}$alkoxy, halo$C_{1-4}$alkoxy, OH, $C_{1-6}$alkyl-$SO_2$— and phenyl-$SO_2$—, the alkyl and phenyl portions of $C_{1-6}$alkyl-$SO_2$— and phenyl-$SO_2$— being optionally substituted with 1-3 halo, $C_{1-3}$ alkyl, halo$C_{1-3}$alkyl, $C_{1-3}$alkoxy and halo$C_{1-3}$alkoxy groups.

3. A compound of formula I:

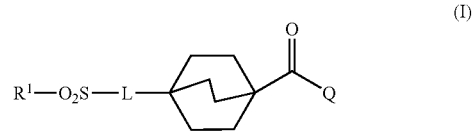

(I)

or a pharmaceutically acceptable salt thereof; wherein:

Q represents $NR^2R^3$ or a group selected from the following:

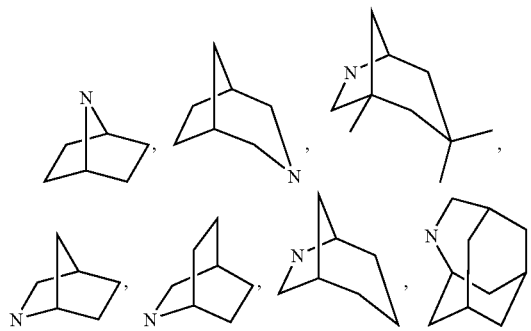

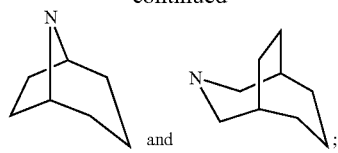

and;

wherein said group may be optionally substituted with from one to five substituents selected from the group consisting of halo, $C_{1-3}$alkyl, $C_{1-3}$alkoxy, $C_{1-3}$haloalkyl and hydroxyl;

L represents the linking group —$(CH_2)_a$—X—$(CH_2)_b$—, wherein:

X represents a bond or is selected from the group consisting of: O, S, NH, N($C_{1-3}$alkyl), C(O)NH, NHC(O), vinyl, Aryl, Aryloxy and HAR, when L is other than a bond, said group L is optionally substituted with 1-5 groups selected from: halo, cyano, $C_{1-4}$alkoxy, $C_{1-4}$alkylthio, hydroxy and amino;

said Aryl, Aryloxy and HAR groups being further optionally substituted with one to five of the following groups: halo, cyano, $C_{1-4}$alkoxy, $C_{1-4}$alkylthio, hydroxy and amino;

when X is O, S, NH or N($C_{1-3}$alkyl), a represents an integer of from 2-6 and b represents an integer of from 0-4, such that the sum of a and b is from 2-6;

and when X is a bond, C(O)NH, NHC(O), vinyl, Aryl, Aryloxy or HAR, a and b each represent integers of from 0-6, such that the sum of a and b is 0 to 6;

$R^1$ represents a member selected from the group consisting of: Aryl or HAR, optionally substituted with one to five of the following groups: halo, cyano, $C_{1-4}$alkoxy, $C_{1-4}$alkylthio, hydroxy, amino, Aryl and HAR, said Aryl and HAR each being further optionally substituted with one to three substituents independently selected from cyano, halo, hydroxy, amino, carboxy, trifluoromethyl, trifluoromethoxy, $C_{1-4}$alkyl, and $C_{1-4}$alkoxy;

$R^2$ is H or $C_{1-3}$alkyl; and $R^3$ is a bicyclic or tricyclic alkyl moiety having 6-12 carbon atoms, optionally substituted with 1-4 substituents selected from the group consisting of $C_{1-4}$alkyl, halo, halo$C_{1-4}$ alkyl, $C_{1-4}$alkoxy, halo$C_{1-4}$alkoxy, OH, $C_{1-6}$alkyl-$SO_2$— and phenyl-$SO_2$—, the alkyl and phenyl portions of $C_{1-6}$alkyl-$SO_2$— and phenyl-$SO_2$— being optionally substituted with 1-3 halo, $C_{1-3}$ alkyl, halo$C_{1-3}$alkyl, $C_{1-3}$alkoxy and halo$C_{1-3}$alkoxy groups.

4. A compound represented by structural formula I $$R^1—O_2S—L—\text{(structure)}—Q$$ (I)

or a pharmaceutically acceptable salt thereof; wherein:

Q represents $NR^2R^3$ or a group selected from the following:

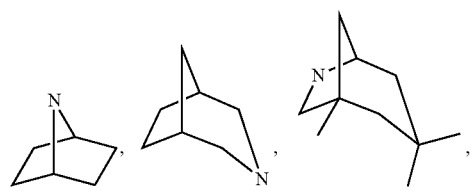

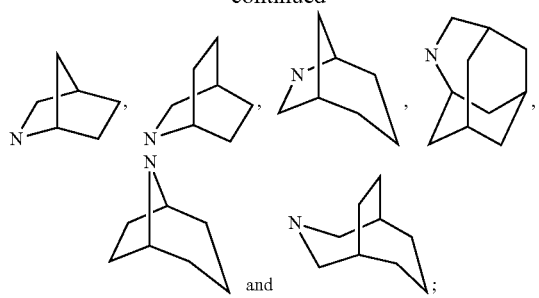

and;

wherein said group may be optionally substituted with from one to five substituents selected from the group consisting of halo, $C_{1-3}$alkyl, $C_{1-3}$alkoxy, $C_{1-3}$haloalkyl and hydroxyl;

L represents the linking group —$(CH_2)_a$—X—$(CH_2)_b$—, wherein:

X represents a bond or is selected from the group consisting of: O, S, NH, N($C_{1-3}$alkyl), C(O)NH, NHC(O), vinyl, Aryl, Aryloxy and HAR, when L is other than a bond, said group L is optionally substituted with 1-5 groups selected from: halo, cyano, $C_{1-4}$alkoxy, $C_{1-4}$alkylthio, hydroxy and amino;

said Aryl, Aryloxy and HAR groups being optionally substituted with 1-5 groups selected from halo, cyano, $C_{1-4}$alkoxy, $C_{1-4}$alkylthio, hydroxy and amino;

when X is O, S, NH or N($C_{1-3}$alkyl), a represents an integer of from 2-6 and b represents an integer of from 0-4, such that the sum of a and b is from 2-6;

and when X is a bond, C(O)NH, NHC(O), vinyl, Aryl, Aryloxy or HAR, a and b each represent integers of from 0-6, such that the sum of a and b is 0 to 6;

wherein $R^1$ represents a $C_{1-4}$alkyl group optionally substituted with 1-3 fluoro groups, or a phenyl group optionally substituted with 1-2 halo, $C_{1-3}$alkyl, mono-, di- or tri-fluoro$C_{1-3}$alkyl or mono-, di- or tri-fluoro$C_{1-3}$alkoxy groups;

$R^2$ is H or $C_{1-3}$alkyl; and $R^3$ is a bicyclic or tricyclic alkyl moiety having 6-12 carbon atoms, optionally substituted with 1-4 substituents selected from the group consisting of $C_{1-4}$alkyl, halo, halo$C_{1-4}$alkyl, $C_{1-4}$alkoxy, halo$C_{1-4}$alkoxy, OH, $C_{1-6}$alkyl-$SO_2$— and phenyl- $SO_2$— the alkyl and phenyl portions of $C_{1-6}$alkyl-$SO_2$— and phenyl-$SO_2$— being optionally substituted with 1-3 halo, $C_{1-3}$alkyl, halo$C_{1-3}$alkyl, $C_{1-3}$alkoxy and halo$C_{1-3}$alkoxy groups.

5. A compound in accordance with claim 4 wherein $R^1$ represents methyl, ethyl, trifluoromethyl, isopropyl, t-butyl, 2,2,2-trifluoroethyl or phenyl optionally substituted with halo, methyl, trifluoromethyl or trifluoromethoxy.

6. A compound in accordance with claim 1 wherein:

L represents —$(CH_2)_a$—X—$(CH_2)_b$—,

X represents a bond, O, S, Aryl, Aryloxy or HAR;

when X represents O or S, a represents an integer having the value of either 2, 3 or 4, and b represents an integer from 0-4 such that the sum of a plus b represents an integer from 2-6, and when X is a bond, Aryl, Aryloxy or HAR, a and b each represent an integer from 0-6 such that the sum of a plus b represents an integer from 0 to 6.

7. A compound in accordance with claim 6 wherein L is selected from the group consisting of: methylene, ethylene, propylene, butylene and 1,4-phenylene.

8. A compound in accordance with claim 1 wherein:

Q represents a member selected from the group consisting of:

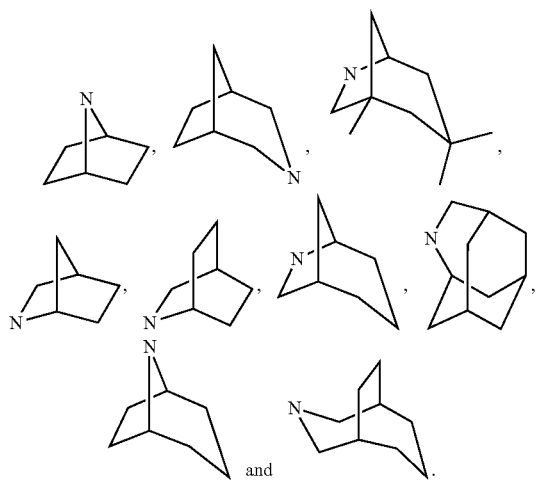

9. A compound in accordance with claim 1 wherein: Q represents $NR^2R^3$.

10. A compound in accordance with claim 9 wherein:
Q represents $NR^2R^3$,
$R^2$ represents H and
$R^3$ represents a bicyclic or tricyclic alkyl moiety having 6-12 carbon atoms, optionally substituted with 1-3 members selected from the group consisting of: $CH_3$, fluoro, chloro, $CF_3$, $OCH_3$, $OCF_3$, and $CH_3SO_2$.

11. A compound in accordance with claim 10 wherein $R^3$ represents 2-adamantyl optionally substituted with 1-3 members selected from the group consisting of: $CH_3$, fluoro, chloro, $CF_3$, $OCH_3$, $OCF_3$, and $CH_3SO_2$.

12. A compound in accordance with claim 10 wherein $R^3$ represents exo-bornyl optionally substituted with 1-3 members selected from the group consisting of: $CH_3$, fluoro, chloro, $CF_3$, $OCH_3$, $OCF_3$, and $CH_3SO_2$.

13. A compound in accordance with claim 4 wherein:
$R^1$ represents a $C_{1-4}$alkyl group optionally substituted with 1-3 fluoro groups, or a phenyl group optionally substituted with 1-2 halo, $C_{1-3}$alkyl, mono-, di- or tri-fluoro$C_{1-3}$alkyl or mono-, di- or tri-fluoro$C_{1-3}$alkoxy groups;
L represents $-(CH_2)_a-X-(CH_2)_b-$,
X represents a bond, O, S, Aryl, Aryloxy or HAR;
when X represents O or S, a represents an integer having the value of either 2, 3 or 4, and b equals represents an integer from 0-4 such that the sum of a plus b represents an integer from 2-6, and
when X is a bond, Aryl, Aryloxy or HAR, a and b each represent an integer from 0-6 such that the sum of a plus b represents an integer from 0 to 6;
Q represents $NR^2R^3$ or is selected from the group consisting of:

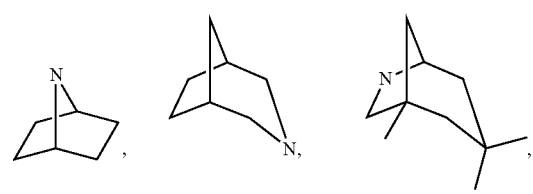

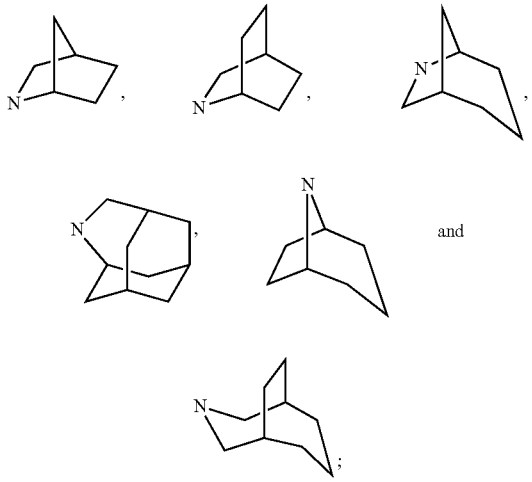

$R^2$ represents H and $R^3$ represents a bicyclic or tricyclic alkyl moiety having 6-12 carbon atoms, optionally substituted with 1-3 members selected from the group consisting of: $CH_3$, fluoro, chloro, $CF_3$, $OCH_3$, $OCF_3$, and $CH_3SO_2$.

14. A compound in accordance with claim 13 wherein:
$R^1$ represents methyl or ethyl, trifluoromethyl, isopropyl, t-butyl, 2,2,2-trifluoroethyl or phenyl optionally substituted with halo, methyl, trifluoromethyl or trifluoromethoxy;
L is selected from the group consisting of: methylene, ethylene, propylene, butylene and 1,4-phenylene,
Q represents $NR^2R^3$ ;
$R^2$ represents H and $R^3$ represents a bicyclic or tricyclic alkyl moiety having 6-12 carbon atoms, optionally substituted with 1-3 members selected from the group consisting of: $CH_3$, fluoro, chloro, $CF_3$, $OCH_3$, $OCF_3$, and $CH_3SO_2$.

15. A compound in accordance with claim 1 selected from the group consisting of:

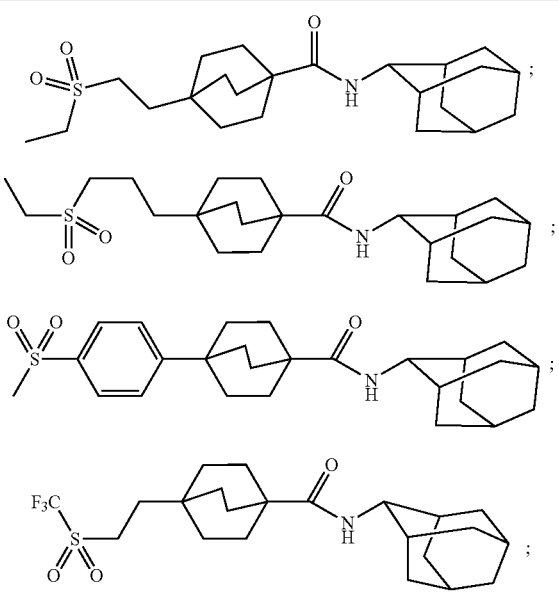

-continued

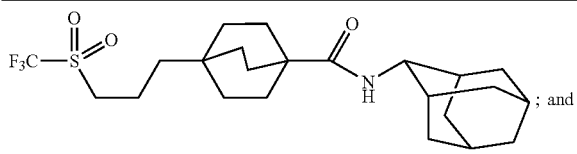; and

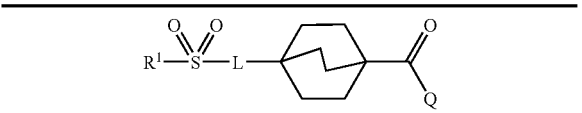

| R¹ | L | Q |
|---|---|---|
| ethyl | ethylene | 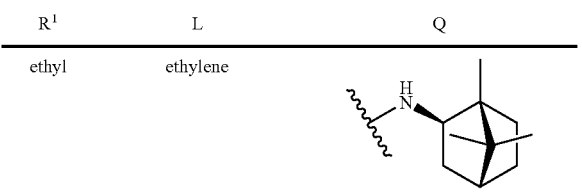 |
| ethyl | ethylene | 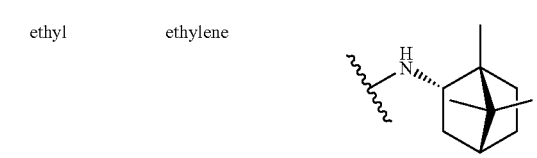 |
| ethyl | ethylene | 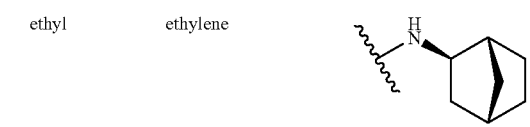 |
| ethyl | ethylene | 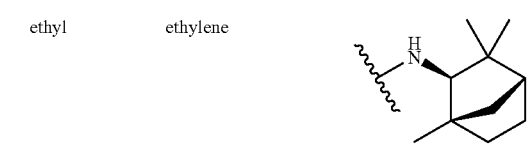 |
| ethyl | ethylene | 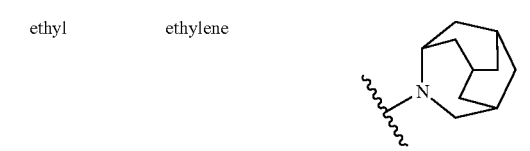 |
| ethyl | ethylene | 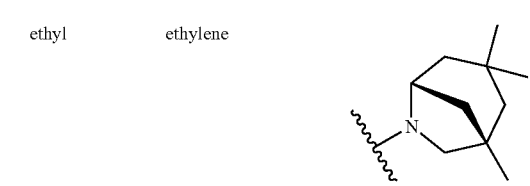 |
| ethyl | ethylene |  |
| ethyl | propylene | 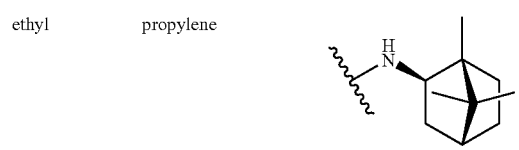 |
| ethyl | methylene | 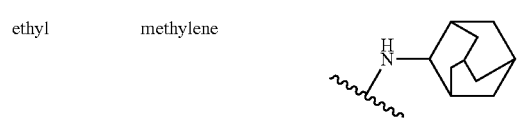 |
| ethyl | methylene | 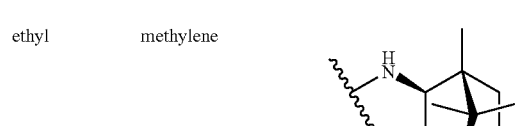 |
| ethyl | methylene | 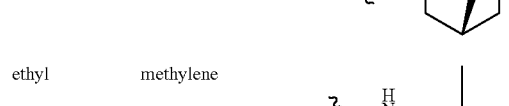 |
| methyl |  | 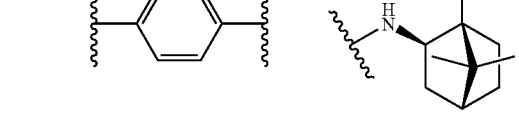 |
| CF₃ | ethylene | 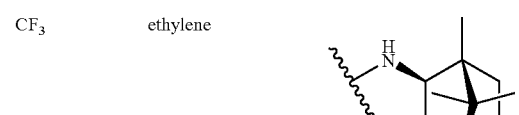 |
| CF₃ | propylene | 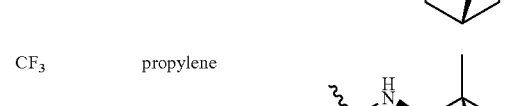 | or a pharmaceutically acceptable salt thereof.

16. A pharmaceutical composition comprising a compound in accordance with claim 1 in combination with a pharmaceutically acceptable carrier.

* * * * *